(12) United States Patent
Ito

(10) Patent No.: US 8,850,904 B2
(45) Date of Patent: Oct. 7, 2014

(54) HORIZONTAL COMPONENT CATCHER OF DUSTFALL IN ATMOSPHERE AND MEASURING METHOD OF HORIZONTAL COMPONENT

(75) Inventor: Nobuaki Ito, Tokyo (JP)

(73) Assignee: Nippon Steel & Sumitomo Metal Corporation, Tokyo (JP)

(*) Notice: Subject to any disclaimer, the term of this patent is extended or adjusted under 35 U.S.C. 154(b) by 267 days.

(21) Appl. No.: 13/260,089

(22) PCT Filed: Apr. 1, 2010

(86) PCT No.: PCT/JP2010/002418
§ 371 (c)(1),
(2), (4) Date: Oct. 18, 2011

(87) PCT Pub. No.: WO2010/113521
PCT Pub. Date: Oct. 7, 2010

(65) Prior Publication Data
US 2012/0024084 A1    Feb. 2, 2012

(30) Foreign Application Priority Data
Apr. 1, 2009    (JP) .................................. 2009-089492

(51) Int. Cl.
*G01N 1/24* (2006.01)
*G01N 1/22* (2006.01)

(52) U.S. Cl.
CPC ............ *G01N 1/2208* (2013.01); *G01N 1/2202* (2013.01); *G01N 1/2273* (2013.01)
USPC ...................................................... 73/863.52

(58) Field of Classification Search
None
See application file for complete search history.

(56) References Cited

U.S. PATENT DOCUMENTS

| 3,953,182 A * | 4/1976 | Roth .......................... 73/863.22 |
| 4,242,908 A | 1/1981 | Tombach |
| 4,762,009 A * | 8/1988 | Scrudto ...................... 73/863.52 |
| 5,040,424 A | 8/1991 | Marple et al. |

(Continued)

FOREIGN PATENT DOCUMENTS

| CN | 101013070 A | 8/2007 |
| JP | 50-74388 U | 6/1975 |

(Continued)

OTHER PUBLICATIONS

CN 101013070 A Aug. 8, 2007.*

(Continued)

*Primary Examiner* — Robert R Raevis
(74) *Attorney, Agent, or Firm* — Birch, Stewart, Kolasch & Birch, LLP

(57) ABSTRACT

A horizontal atmospheric dustfall component trap includes: a dust sampling port that includes a ceiling plate, a side wall, and four or more partition plates; an air pipe; and a trap container, wherein the side wall is a plate that has a vertical center axis and has a side surface having a shape of a substantially circular truncated cone or a polygonal truncated cone widened upward, wherein the side wall is provided with four or more external air inlets each having an opening disposed at the same interval in the circumferential direction of the side wall and disposed at a specific height near the upper end thereof, and wherein the four or more partition plates divide a space surrounded by the side wall into fan-shaped areas having an equal size in a horizontal cross-section.

9 Claims, 12 Drawing Sheets

CROSS-SECTIONAL VIEW ALONG A-A

CROSS-SECTIONAL VIEW ALONG B-B

(56) References Cited

U.S. PATENT DOCUMENTS

| | | | |
|---|---|---|---|
| 5,224,059 A | | 6/1993 | Nitta et al. |
| 5,412,975 A | * | 5/1995 | Raabe et al. ............. 73/28.04 |
| 5,607,497 A | * | 3/1997 | Brown ................. 73/864.71 |
| 2004/0038385 A1 | | 2/2004 | Langlois et al. |
| 2004/0055362 A1 | | 3/2004 | Shinohara et al. |
| 2005/0279181 A1 | * | 12/2005 | Trakumas et al. ......... 73/863.22 |
| 2012/0024084 A1 | | 2/2012 | Ito |

FOREIGN PATENT DOCUMENTS

| | | |
|---|---|---|
| JP | 56-31618 A | 3/1981 |
| JP | 60-185244 U | 12/1985 |
| JP | 62-119647 U | 7/1987 |
| JP | 62-124543 U | 8/1987 |
| JP | 63-60981 U | 4/1988 |
| JP | 1-307614 A | 12/1989 |
| JP | 1-307814 A | 12/1989 |
| JP | 2-40212 A | 2/1990 |
| JP | 4-136551 U | 12/1992 |
| JP | 5-187988 A | 7/1993 |
| JP | 5-187989 A | 7/1993 |
| JP | 6-21848 B2 | 3/1994 |
| JP | 9-89727 A | 4/1997 |
| JP | 9-210942 A | 8/1997 |
| JP | 2001-50870 A | 2/2001 |
| JP | 2002-82038 A | 3/2002 |
| JP | 2002-333396 A | 11/2002 |
| JP | 2004-144664 A | 5/2004 |
| JP | 3574045 B2 | 10/2004 |
| JP | 2006-3090 A | 1/2006 |
| JP | 2006-508371 A | 3/2006 |
| JP | 2008-304277 A | 12/2008 |

OTHER PUBLICATIONS

JP 60-185244 U Dec. 9, 1985.*
JP 62-119647 U Jul. 29, 1987.*
JP 62 124543 U Aug. 7, 1987.*
JP 63-60981 U Apr. 22, 1988.*
Chinese Office Action mailed Dec. 14, 2012 in Chinese Patent Application # 201080015478.1.*
International Search Reprt for PCT/JP 2010/0024218, mailed Jun. 22, 2010.*
Metropolitan Acid Rain: written b y Laboratory for Environmental Chemistry, Department of Chemistry, Keio University, 2003, Kkeio University Press Inc. (Tokyo).*
"Low volume air sampler", Japanese Industrial Standard, JIS Z 8814, 1994, 27 pages.
Goossens et al., "Wind tunnel and field calibration of six aeolian dust samplers", Atmospheric Environment, vol. 34, 2000, pp. 1043-1057.
Harrison et al., "Atmospheric Particles", IUPAC Series on Analytical and Physical Chemistry of Environmental Systems, vol. 5, 1998, 17 pages.
International Search Report with English translation dated Jun. 22, 2010, for Application No. PCT/JP2010/002418.
Laboratory for Environmental Chemistry, "Metropolitan Acid Rain", 2003, 131 pages.
Chinese Office Action and Search Report, dated Dec. 14, 2012, for Chinese Application No. 201080015478.1, including English translation of Search Report only.
International Search Report for PCT/JP2010/002416, mailed Jun. 22, 2010.
U.S. Office Action for U.S. Appl. No. 13/259,994 mailed Apr. 3, 2013.

* cited by examiner

CROSS-SECTIONAL VIEW ALONG A-A

SUCTION

SUCTION

SUCTION

CROSS-SECTIONAL VIEW

CROSS-SECTIONAL VIEW ALONG A-A

CROSS-SECTIONAL VIEW ALONG B-B

CROSS-SECTIONAL VIEW ALONG A-A

CROSS-SECTIONAL VIEW ALONG B-B

CROSS-SECTIONAL VIEW ALONG A-A

CROSS-SECTIONAL VIEW ALONG B-B

HORIZONTAL COMPONENT CATCHER OF DUSTFALL IN ATMOSPHERE AND MEASURING METHOD OF HORIZONTAL COMPONENT

TECHNICAL FIELD

The present invention relates to an atmospheric dustfall trapping device (catcher) and a dustfall amount measurement method using the device, and particularly, to a horizontal dustfall component trap and a horizontal dustfall component amount measurement method.

Priority is claimed on Japanese Patent Application No. 2009-089492, filed on Apr. 1, 2009, the content of which is incorporated herein by reference.

BACKGROUND ART

In the description of the related art and the description of the invention, the correlation between components denoted by the same reference numerals does not indicate that the configurations and functions thereof are the same, but merely indicates a partial correlation in function or general design. Even when specific configurations or functions are significantly different, the same reference numerals may be used.

Various atmospheric dust is produced in manufacturing processes and consumers activities. Among them, dusts with a diameter of more than approximately 10 μm is called dustfall, which can present in the atmosphere in a free-falling status. Dustfall is a significant environmental problem, and investigations and countermeasures need to be put in place. In order to determine the true dustfall situation, it is important to accurately measure the amount of dustfall. Therefore, a device for accurately trapping dustfall is needed.

Comparatively large particles in the atmosphere, for example, dustfall which has particles having a diameter of more than 10 μm, do not completely follow the ambient atmospheric flow, and fall in the atmosphere at a different speed in accordance with the density or the size of the particle of the dustfall to be deposited on the ground. When there is a barrier in the atmosphere, the dustfall collides with the barrier and adheres thereto. For this reason, the environmental influence of the dustfall mainly occurs due to pollution caused by the dustfall deposited and adhering to a specific object. Therefore, in order to evaluate the environmental influence of the dustfall, a simple measurement of the concentration of the dustfall in the atmosphere is not sufficient, and the amount of dustfall passing through a unit area of an inspection surface fixed in a space per hour, that is, the flux of the dustfall needs to be measured.

The flux of the dustfall which is the cause of environmental problems may be divided into a vertical flux and a horizontal flux. In the vertical flux, the inspection surface is horizontal, and is mainly in relation to the evaluation of the deposition of the dustfall on the ground. In the horizontal flux, the inspection surface is vertical, and mainly relates to the evaluation of the adherence of the dustfall to a vertical surface such as a wall of a building. The atmospheric flow outside a building, that is, wind may be regarded as having a vector in the horizontal plane according to an average for a long period of time. For this reason, the vertical flux is not influenced by the wind speed. In contrast, the horizontal flux is a function of the wind speed. More specifically, the flux of the dustfall may be defined by the following equation.

[vertical flux of dustfall]=[concentration of dustfall]×[falling speed of dustfall]

[horizontal flux of dustfall]=[concentration of dustfall]×[wind speed of vertical component of inspection surface]

Likewise, in order to measure the horizontal dustfall flux, there is a need to recognize the wind direction or the wind speed during measurement at all times. Furthermore, the measurement device needs to have a function of trapping the flow of the dustfall in the wind direction at all times. On the other hand, in the measurement of the vertical flux of the dustfall, such consideration is not needed, and the horizontal dustfall flux may be measured in a simpler manner. For this reason, in the public management of the dustfall, a device solely measuring the vertical flux, for example, a deposit gauge shown in FIG. 1 has been used. In the deposit gauge, a dust sampling port 1 is formed in a trumpet shape which is opened upward. The dustfall is trapped in a manner such that the dustfall falling and deposited on the inner surface of the dust sampling port 1 is made to flow into a trap container 25 present below the dustfall sampling port 1 by rainwater or water used for collecting the trapped dustfall.

Further, the horizontal dustfall flux may be formally transformed from the vertical flux in the following equation.

[horizontal flux of dustfall]=[vertical flux of dustfall]×[wind speed of vertical component of inspection surface]/[falling speed of dustfall]

Here, the wind speed of the vertical component of the inspection surface is defined as below. First, an imaginary inspection plane is vertically installed at a point which causes a problem. At this time, the wind speed of the vertical component of the inspection surface is a component in accordance with the direction perpendicular to the inspection plane in the wind speed at the point.

For this reason, even when the horizontal dustfall flux is regarded as a problem, a simple evaluation using the measurement result of the vertical flux and the equation has been conducted. However, in fact, it is difficult to quantitatively measure the falling speed of the dustfall variously changing with time, and a large error occurs when calculating the horizontal dustfall flux on the basis of the equation. Therefore, when the horizontal flux is a problem, it is desirable to directly measure the horizontal flux from the viewpoint of measurement precision. In order to directly measure the horizontal dustfall flux, generally, a method is known in which a horizontal component of dustfall is trapped by a certain trapping device and the trapped amount is converted into a horizontal dustfall flux by using values of the trap time, the opening area of the trapping device, and the like.

Here, the horizontal dustfall component amount will be described. The form of adherence (deposition) of the dustfall may be divided into a vertical dustfall component in which the dustfall adheres to a horizontal surface such as a ground surface from the upside thereof and a horizontal dustfall component in which the dustfall adheres to a vertical surface such as a wall or a window of a building from the side surface thereof. In the case of large particles such as dustfall, the vertical component and the horizontal component may be defined as the amount of the dustfall passing through an imaginary horizontal plane (in the case of the vertical flux) or an imaginary vertical plane (in the case of the horizontal flux) set in the atmosphere. The vertical dustfall component amount or the horizontal dustfall component amount may be respectively converted into the vertical flux or the horizontal dustfall flux by dividing the amount of the dustfall passing through the imaginary plane by the passage time and the imaginary area.

As a method of directly measuring the horizontal dustfall component amount, there are two types, a horizontal dustfall component trap method and a uniform suction method.

The horizontal dustfall component trap method which is a first method of directly measuring the horizontal dustfall component will be described. In this method, the external air inlet of the dust sampling port is disposed to be substantially perpendicular to the horizontal plane. The wind present in the external air is naturally introduced from the external air inlet of the dust sampling port together with the dustfall in the external air. Next, the dustfall is separated from the external air inside the dust sampling port so as to be trapped in the trap container connected to the dust sampling port. Furthermore, the dustfall trapped in the trap container is collected and the mass thereof is measured. From this result, the trapped dustfall amount per hour is obtained. The horizontal dustfall flux is calculated from the trapped dustfall amount and the opening area of the dust sampling port.

In general, since a device of this method does not need a power mechanism or a control mechanism, the configuration of the device is simple. In order to accurately trap the horizontal dustfall component, an ideal structure may be supposed as follows: in the horizontal dustfall component trap, the external air inlet is made to be perpendicular to the wind direction of the external air; the atmosphere introduction flow speed of the external air inlet is made to be substantially equal to the wind speed of the external air; and the dustfall flowing into the dust sampling port is separated from the atmosphere flowing out from the device as much as possible so as to be stored inside the device. The horizontal dustfall component indicates a horizontal movement flow of the dustfall due to the wind in the external air. The amount of the horizontal dustfall component trapped per hour and for each opening area of the external air inlet is the horizontal dustfall amount flux.

Likewise, in the ideal horizontal dustfall component trap, the trapped horizontal dustfall component amount is proportional to the horizontal dustfall flux amount at the trap position at all times. For this reason, wind speed information is not necessary when obtaining the horizontal dustfall flux amount, and the structure of the device and the analysis method may be simplified. This point is a great benefit of the horizontal dustfall component trap method compared to the other measurement methods requiring local wind speed information.

However, such an ideal horizontal dustfall component trap is hypothetical, and it is difficult to satisfy all the above-described conditions for realizing the ideal horizontal dustfall component trap in the actual horizontal dustfall component trap. For this reason, in the actual horizontal dustfall component trap, the horizontal dustfall component trap amount becomes a value smaller than the ideal horizontal dustfall component amount converted from the local and actual horizontal dustfall amount flux.

The ratio of the horizontal dustfall component trap amount of a specific horizontal dustfall component trap with respect to the ideal horizontal dustfall component trap amount is called dustfall trapping efficiency. The dustfall trapping efficiency for each device may be obtained by an experiment. In this case, the mass of the dustfall may be measured by the gauge and the measurement value may be corrected by using the dustfall trapping efficiency. Accordingly, even when the dustfall trapping efficiency of the gauge is not 100%, the horizontal dustfall flux may be highly precisely obtained through the measurement using the horizontal dustfall component trap. Further, when only the relative relationship between the horizontal dustfall amount flux at a plurality of points and time points is taken into consideration, the ideal horizontal dustfall component trap amount does not need to be essentially considered. In this case, the ratio of the actual horizontal dustfall component trap amount with respect to the predetermined standard trap amount may be obtained, and this value may be used to manage the tendency of the horizontal dustfall flux.

Even in the method of using the horizontal dustfall component trap, the benefit, in which the tendency of the horizontal dustfall amount flux is measured without the local wind speed information, of the horizontal dustfall component trap method is not basically degraded. However, in the case of the trap having low dustfall trapping efficiency, the device needs to be increased in size in order to obtain the mass of the dustfall minimally necessary for measuring the mass determined by the mass measurement method. Further, in the case of the trap of which the dustfall trapping efficiency largely changes due to the weather condition, since it is difficult to highly precisely perform correction when obtaining the horizontal dustfall flux, the measurement precision degrades. Therefore, in the horizontal dustfall component trap, the dustfall trapping efficiency needs to be high and stable. Hereinafter, the type of the specific horizontal dustfall component trap will be described.

As the trap for the horizontal dustfall flux, a device is disclosed in which wind naturally circulates inside a dust sampling port, a part of dustfall contained in the introduced wind is trapped by inertia or gravity to trap the dustfall, and a horizontal dustfall flux is measured according to the result. As this type, Non-patent Document 1 discloses a plurality of particle traps. As a representative type, a big spring number eight (BSNE) is shown in FIGS. 2A and 2B.

In the BSNE, the atmosphere naturally flowing from an external air inlet 10 into the dust sampling port 1 is decelerated inside the device as the passage is widened. Subsequently, as depicted by a flow line of an atmospheric flow 17 passing through the dust sampling port, the atmosphere naturally flows outward from an exhaust port 8 as a metallic mesh provided on the top surface of the device. The wind decelerates inside the dust sampling port, so that the staying time of the dustfall inside the dust sampling port 1 increases, and the dustfall freely falls by a long distance inside the dust sampling port in the meantime. Likewise, since the wind speed inside the dust sampling port becomes slower than the wind speed of the flow 15 of the external air, the staying time of the dustfall inside the dust sampling port 1 increases. As described above, the portion inside the dust sampling port 1 exhibiting an effect of increasing the falling distance of the dustfall may be called a wind reduction area 13. The atmospheric dustfall freely falling in the wind reduction area 13 freely falls or collides with the wall of the downstream end of the device when passing through the inside of the device as depicted by the flow line of the trapped dustfall 19, and passes through the metallic mesh 30 provided below the passage to be deposited and trapped in a particle trap 44.

A part of the dust inside the dust sampling port 1 flows into the external air from the exhaust port 8 as depicted by the flow line of dustfall 20 passing through the dust sampling port. Further, the entire device is rotatable in the horizontal direction, and the external air sampling port 10 is made to be automatically directed toward the upward wind direction at all times due to the action of a blade 23 and a rotary shaft 24 provided in the device. Since this device includes a mechanism automatically turning the external air inlet 10 in accordance with the wind direction, there is a problem in that the structure becomes complex and tends to increase in size as the horizontal dustfall component trap. Further, in this device, since the dustfall may not be always efficiently separated from the atmosphere inside the dust sampling port 1, as disclosed in Non-patent Document 1, the dustfall trapping efficiency is not high.

Non-patent Document 1 introduces a suspended sediment trap (SUSTRA) or a Modified Wilson & Cooke sampler (MWAC) as the trap for the horizontal dustfall flux. The trap principle of the SUSTRA is basically the same as that of the BSNE. The MWAC dust sampler shown in FIGS. 7A and 7B includes: a trap bottle with an external air inlet 10 which is an L-shaped pipe having an opening provided in the upward wind direction; and an exhaust port 8 which is an L-shaped pipe having an opening provided in the downward wind direction. The MWAC does not have a special mechanism that makes the external air inlet 10 of the dust sampling port follow the wind direction. For this reason, this is not suitable for a trap that traps the horizontal dustfall component for a long time in the external air of which the wind direction and the wind speed change all the time.

The uniform suction method which is a second method of directly measuring the horizontal dustfall component will be described.

In this method, the instant wind direction and the instant wind speed are measured. Further, the external air inlet of the dust sampling port is made to be perpendicular to the wind direction in the horizontal plane at all times. Furthermore, in the external air inlet, the external air containing the dustfall is suctioned at the same speed as that of the wind speed of the external air. Furthermore, the suctioned atmospheric dustfall is trapped by a trap filter or the like. As a result, the mass of the dustfall trapped per hour is measured, and the horizontal dustfall flux including the measurement value and the opening area of the external air inlet is calculated. In the case of realizing this method, generally, a device includes a power mechanism and a control mechanism suctioning the external air and changing the direction of the external air inlet.

Next, the principle of measuring the horizontal dustfall flux using the uniform suction method will be described. Generally, the dustfall which includes large particles does not completely follow the flow of the wind. In the dust sampling port 1 of the dustfall amount measurement device, the suction may be performed in the direction different from the wind direction as shown in FIG. 3 or the suction may be performed at a speed different from the wind speed as shown in FIG. 4. In such a case, it is not limited to a case in which the dustfall in the external air is suctioned to the dust sampling port 1 together with suctioned atmosphere 16. As in the dustfall 18 in the external air of FIGS. 3 and 4, the ratio of the dustfall bypassing the external air inlet 10 is too large to be ignored. Furthermore, the ratio of the bypassing dustfall is sensitively influenced by various weather conditions, characteristics of the dustfall, and the shape of the device. For this reason, it is difficult to predict the ratio of the bypassing dustfall. Therefore, the suction type shown in FIGS. 3 and 4 is not desirable as the dustfall trap method for measuring the horizontal dustfall flux. Specifically, such a dustfall sampling method is shown in Patent Documents 1, 2, and the like. In these devices, since the external air suction speed is constant in the external air inlet 10 at all times, the wind speed of the external air is generally not equal to the external air introduction speed. Further, the direction of disposing the external air inlet 10 is generally fixed in many cases. Therefore, the normally changing wind direction of the external air is not generally equal to the direction of the external air inlet 10. For this reason, as disclosed in Non-patent Document 4, the dust trapping efficiency of the particle (that is, a particle which is equal in size to the dustfall) having a diameter more than 10 μm in this type of dust sampling port 1 is extremely small so as to be several % or less. Further, since the dust trapping efficiency is strongly influenced by the ambient measurement condition such as a wind speed, it is difficult to highly precisely recognize the outdoor dust trapping efficiency. For this reason, in the external air inlet 10 of the dust sampling port 1 trapping the atmospheric dustfall in order to measure the horizontal dustfall flux, there is a need to provide a method of introducing atmosphere at substantially the same speed as the wind speed and the wind direction of the external air, that is, a uniform suction method.

As a specific example of the uniform suction method, a method is disclosed in Patent Document 2. A structure of a device using this method will be described by referring to FIG. 16. External air containing dustfall is suctioned from the external air inlet 10 using a blower or a compressor 7, and only the dustfall is trapped by a trap filter 35. The atmosphere obtained by removing the dustfall is discharged to the outside of the system from the exhaust port 8. The atmosphere containing the dustfall is suctioned to the dust sampling port 1 in a manner such that the wind speed of the external air is measured by an aerovane 31 and the suction flow rate of the blower or the compressor 7 is controlled so that the atmosphere introduction speed at the inlet of the dust sampling port 1 is equal to the wind speed at all times. The uniform suction is mainly applied when measuring the flux of the dustfall inside a gas duct of which the wind direction is fixed. In order to recognize the horizontal dustfall flux, the wind speed is controlled when applying the uniform suction to the dustfall trap at the outdoor place, and further the direction of the dust sampling port 1 is controlled so that it is aligned with the wind direction at all times. This method is disclosed in Patent Documents 4 and 5. Such a method is the most reliable method of trapping the dustfall in relation to the horizontal flux measurement.

However, in this case, the configuration and the control of the device become complex, and the device may easily become expensive and increased in size. For this reason, this may be mentioned as a simple measurement method.

Further, a low volume sampler shown in Non-patent Document 3 or a high volume sampler obtained by increasing the suction flow rate of the low volume sampler is combined with a separate aerovane, and the direction of the external air inlet and the suction flow speed may be manually corrected at all times, which may be applied in principle to the uniform suction. In this device, the suctioned atmospheric dustfall is filtered by a filter, and a change in weight of the filter is measured off-line so as to calculate the mass of the trapped dustfall. However, with this type, since an operator needs to continuously operate the device, this type is not practical as a method of measuring the horizontal dustfall flux for a long period of time.

Further, in a case where the purpose is the opposite of that of the trapping of the dustfall, that is, in a case where a suspended particulate matter (SPM) which is a minute atmospheric particle (for example, with a diameter of 10 μm or less) is desired to be separated from the dustfall to be trapped, it is desirable to adopt a dust sampling port structure in which the uniform suction state occurs as little as possible. From this viewpoint, in the case of an available SPM measurement device suctioning the external air and measuring the concentration of the SPM in the atmosphere, in order to suppress the suction of the dustfall, a dust sampling port having a shape shown in FIGS. 6A and 6B disclosed in Patent Document 3 may be adopted. The dust sampling port of FIGS. 6A and 6B includes a structure 14 that disturbs the flow inside the dust sampling port in order to suction a large particle to the air port 9 as the SPM close to 10 μm. The dust sampling port is provided on the assumption that the port is applied to an SPM measurement device used for a measurement subject which is a particle having a diameter of 10 μm or less. For this reason, the trapping of the dustfall which is a particle having a diameter more than 10 μm is not considered. For this reason, most of the dustfall flowing into the dust sampling port is directly discharged to the outside of the system through a path denoted by the reference numeral 20 in the drawing. As a result, in the case of the dust sampling port with this shape, the dustfall trapping efficiency is extremely low so as to be 5% or less as shown in Non-patent Document 4. Therefore, this shape is not suitable for collecting the dustfall.

Next, wet deposit and dry deposit of the dustfall will be described. As a physical mechanism used for when the particle of the dustfall is deposited on the ground surface or the wall surface, there are two types, that is, dry deposition of depositing only the particle of the dustfall and wet deposition of depositing the particle of the dustfall received by rain together with a raindrop. The dustfall trapped in the case of rain may be largely classified as a wet deposit, and the dustfall deposited in the case of no rain may be largely classified as a dry deposit. Even in the dustfall of the same type and size, the influence on the environment or the scattering range from the dustfall generating source is different depending on whether it is the dry deposit or the wet deposit, and there is a demand for separating the dustfall into the dry deposit and the wet deposit and trapping in this state from the viewpoint of the environmental management.

Further, the dustfall may be classified from the viewpoint of water solubility, and may be divided into soluble dustfall and insoluble dustfall. In the soluble dustfall and the insoluble dustfall, the main components of the dustfall are different from each other, so that there is a difference in environmental influence. For this reason, in the public administration, the dustfall is managed generally for each of the separate two. Therefore, the dustfall may be classified into four types, that is, dry soluble deposit, dry insoluble deposit, wet soluble deposit, and wet insoluble deposit. In accordance with the classification, it is desirable to trap the dustfall from the viewpoint of the management of the dustfall.

In the vertical dustfall component trap, as a method of realizing the four types of classification, a precipitation sampler with a structure shown in FIG. 5 is available in the market. In this device, a wet deposit dust sampling port 38 and a dry deposit dust sampling port 39 are provided above a wet deposit trap container 36 and a dry deposit trap container 37, and a dust sampling port cover 40, a cover opening and closing mechanism, a cover opening and closing control device 41, a rain detector 42, and a device protection casing 43 are provided above the sampling ports. When the rain detector 42 detects rainfall in the case of rain, the cover opening and closing control device operates the cover opening and closing device so that the dry deposit dust sampling port 39 is blocked by the dust sampling port cover 40. At this time, the wet deposit dust sampling port 38 is opened to the external air, and the dustfall as a wet deposit falls and flows into the wet deposit dust sampling port 38 together with raindrops so as to be trapped in the wet deposit trap container 36. In the case of no rainfall, the dustfall as a dry deposit is trapped in the dry deposit trap container 37 by opening and closing the dust sampling port cover 40 in the sequence opposite to the above-described sequence. In the case of this device, since a sensor such as a rain detector or an opening and closing control device is needed, the structure is complex and power is needed. Further, since the rainfall does not flow into a dry deposit sampling port 1 as not in the deposit gauge, the particle adhering to the inner surface of the dust sampling port is not cleaned to be dropped into the container bottom, and there is a problem in that the dry deposit trap amount significantly reduces since the dry deposits fly again due to wind blowing when opening the dust sampling port cover 40.

On the other hand, in the horizontal dustfall component trap, the dustfall may be trapped regardless of the presence of the rainfall. However, a device that traps the horizontal dustfall component on the basis of the presence of the rainfall as in the rain sampler was not present in the past. When the particle sampling port and the exhaust port are made to be opened and closed by detecting rainfall in the same manner as the rainfall sampler, in principle, it is considered that the horizontal dustfall component becoming wet deposit and dry deposit may be separately trapped. However, as shown in the BSNE, the horizontal dustfall component trap rotates the dust sampling port in accordance with the wind direction in many cases. For this reason, when the cover opening and closing mechanism or the measurement control device are further provided, the device and the control becomes more complicated than the rainfall sampler, which may not be considered as an efficient method. Further, in the horizontal dustfall component trapping device trapping the dustfall using an air filter such as a high volume sampler through the uniform suction method or the like, when raindrops adhere to the filter in the case of strong rainfall, an air suction resistance of the filter rapidly increases, so that a problem arises in that it is difficult to continue the suction. For this reason, such a trapping device is not actually suitable for trapping the wet deposit.

In the component analysis for a minute amount of dustfall, for example, as shown in Non-patent Document 5, generally, an ion chromatography method using an available ion chromatography analysis device or an available fluorescent X-ray method using an available fluorescent X-ray analysis device is used.

RELATED DOCUMENTS

Patent Document

[Patent Document 1] Japanese Unexamined Patent Application, First Publication No. 2006-3090

[Patent Document 2] Japanese Patent Publication No. 3574045

[Patent Document 3] Japanese Unexamined Patent Application, First Publication No. 2004-144664

[Patent Document 4] Japanese Unexamined Utility Model Application, First Publication No. H4-136551

Non-Patent Literature

[Non-patent Document 1] Goossens, D., Offer, Z. Y.: Atmospheric Environment, vol. 34 (2000), pp. 1043-1057

[Non-patent Document 2] Japanese Industrial Standards, JIS Z 7151

[Non-patent Document 3] Japanese Industrial Standards, JIS Z 8814

[Non-patent Document 4] R. M. Harrison, R. E. van Grieken: Atmospheric Particles, John Wiley & Sons (England), 1998, pp. 47-53

[Non-patent Document 5] Metropolitan Acid Rain: written by Laboratory for Environmental Chemistry, Department of Chemistry, Keio University, 2003, Keio University Press Inc. (Tokyo)

SUMMARY OF INVENTION

Technical Problem

As described above, the devices measuring the horizontal dustfall flux of the related arts all had low dustfall trapping efficiency, were expensive, or had a complex structure. Further, there was no method of separating the horizontal dustfall component into a wet deposit and a dry deposit.

It is an object of the invention to provide a cheap horizontal atmospheric dustfall component trap having high dustfall trapping efficiency and having a small and simple structure.

Further, it is an object of the invention to provide a method of separating a horizontal dustfall component into a wet deposit and a dry deposit.

Means for Solving the Problem

As a result of the inventor's study of dustfall measurement, the following solution was contrived.

(1) According to an aspect of the invention, there is provided a horizontal atmospheric dustfall component trap including: a dust sampling port that includes a ceiling plate, a side wall, and four or more partition plates; an air pipe; and a trap container that collects dustfall, flowing from the dust sampling port, through the air pipe, wherein the dust sampling port is connected to the air pipe, wherein the air pipe is connected to the trap container, wherein the lower end of the side wall is provided with an air port as an opening, wherein the air port is connected to the air pipe, wherein the side wall is a plate that has a vertical center axis and has a side surface having a shape of a substantially circular truncated cone or a polygonal truncated cone widened upward, wherein the side wall is provided with four or more external air inlets each having an opening disposed at the same interval in the circumferential direction of the side wall and disposed at a specific height near the upper end thereof, wherein the ceiling plate has a substantially disk shape, wherein the center axis of the ceiling plate is aligned with the center axis of the side wall, wherein the ceiling plate is connected to the upper end of the side wall so as to come into contact therewith, wherein each of the four or more partition plates is a flat plate disposed in a vertical plane, wherein each of the four or more partition plates is connected to the side wall and the ceiling plate without any gap formed therebetween, wherein the four or more partition plates are connected to each other on the center axis of the ceiling plate, and wherein the four or more partition plates divide a space surrounded by the side wall into fan-shaped areas having an equal size in a horizontal cross-section.

(2) In the horizontal atmospheric dustfall component trap of (1), a diameter of the ceiling plate may be larger than a diameter of the upper end of the side wall in the horizontal cross-section, and the ceiling plate may have a peak portion that extends outward from the upper end of the side wall in the circumferential direction.

(3) In the horizontal atmospheric dustfall component trap of (1), a diameter of the ceiling plate may be equal to a diameter of the upper end of the side wall in the horizontal cross-section.

(4) According to an aspect of the invention, there is provided a horizontal atmospheric dustfall component trap including: a first trap which is the horizontal atmospheric dustfall component trap of (3); and a second trap which is the horizontal atmospheric dustfall component trap of (2).

(5) In the horizontal atmospheric dustfall component trap of (2), the radial length of the peak portion of the ceiling plate may satisfy: (the radial length of the peak portion of the ceiling plate)<(the representative wind speed of the external air)/(the free falling speed of dustfall which is desired to be trapped)×(the vertical length between the lower surface of the ceiling plate and the lower end of the air port) and, (the radial length of the peak portion of the ceiling plate)>(the representative wind speed of the external air)/(the free falling speed of a raindrop with a minimum diameter which is not desired to be trapped)×(the vertical length between the lower surface of the ceiling plate and the lower end of the air port).

(6) According to an aspect of the invention, there is provided a horizontal atmospheric dustfall component measurement method using the horizontal atmospheric dustfall component trap of any one of (1) to (3), wherein a value obtained by dividing the amount of dustfall trapped in the horizontal component trap per hour by an effective opening area of the external air inlet is calculated as the horizontal dustfall flux.

(7) There is provided the measurement method of (4) including setting the amount of dustfall trapped by the second trap as an amount of a dry deposit of a horizontal dustfall component; and calculating the amount of the dustfall, which is a remainder obtained by reducing the amount of the dustfall trapped by the second trap from the amount of the dustfall trapped by the first trap, as the amount of a wet deposit of the horizontal dustfall component.

Advantageous Effects of Invention

According to the invention, it is possible to provide a horizontal dustfall component trap capable of measuring a horizontal flux of dustfall with a structure which is small, simple, and cheap. Further, according to one aspect of the invention, a horizontal dustfall component as a dry deposit and a horizontal dustfall component as a wet deposit may be separated from each other.

DESCRIPTION OF EMBODIMENTS

Figure 1:
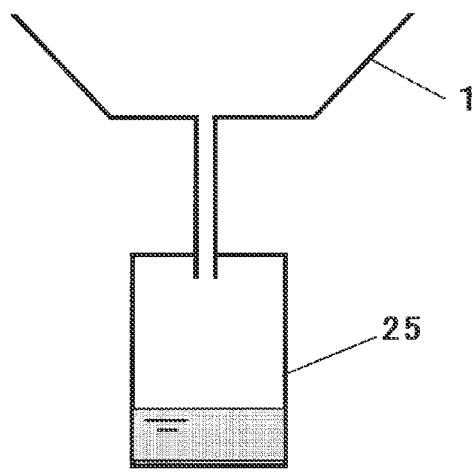
FIG. 1 is a schematic diagram of a related art.
Figure 2A:
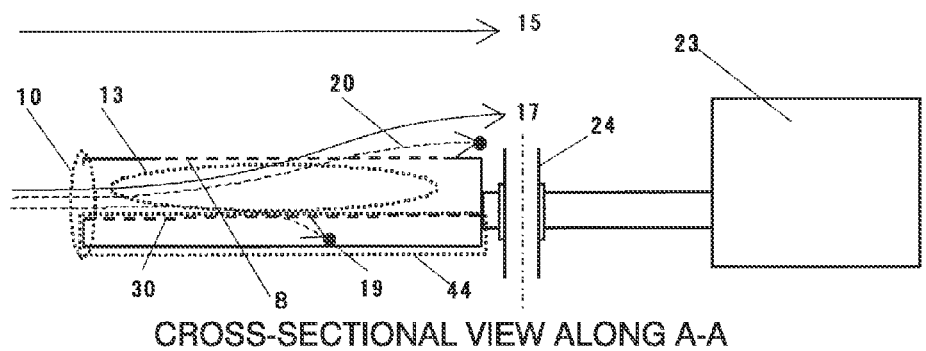
FIG. 2A is a schematic cross-sectional view of another related art.
Figure 2B:
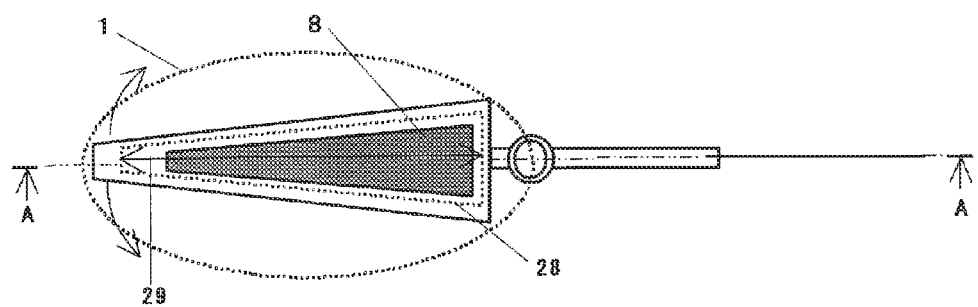
FIG. 2B is a schematic plan view of another related art.
Figure 3:
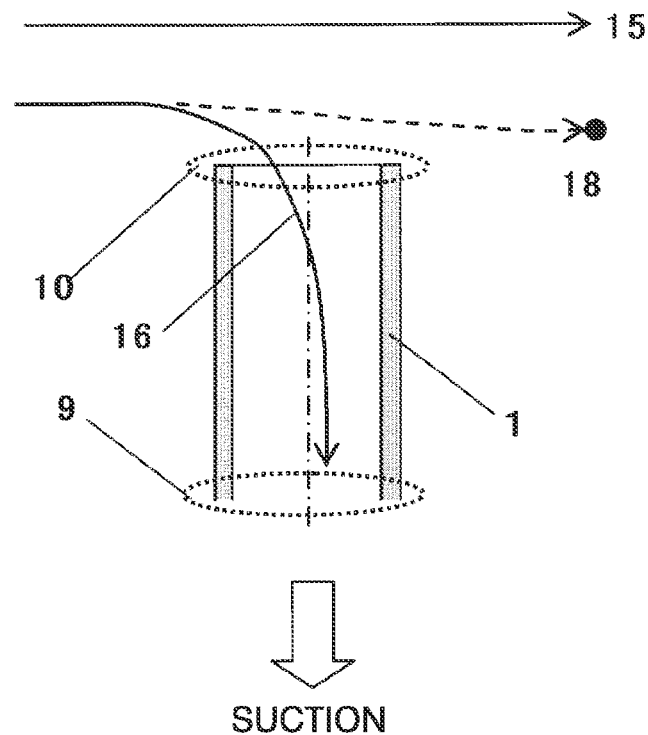
FIG. 3 is a schematic diagram of another related art.
Figure 4:
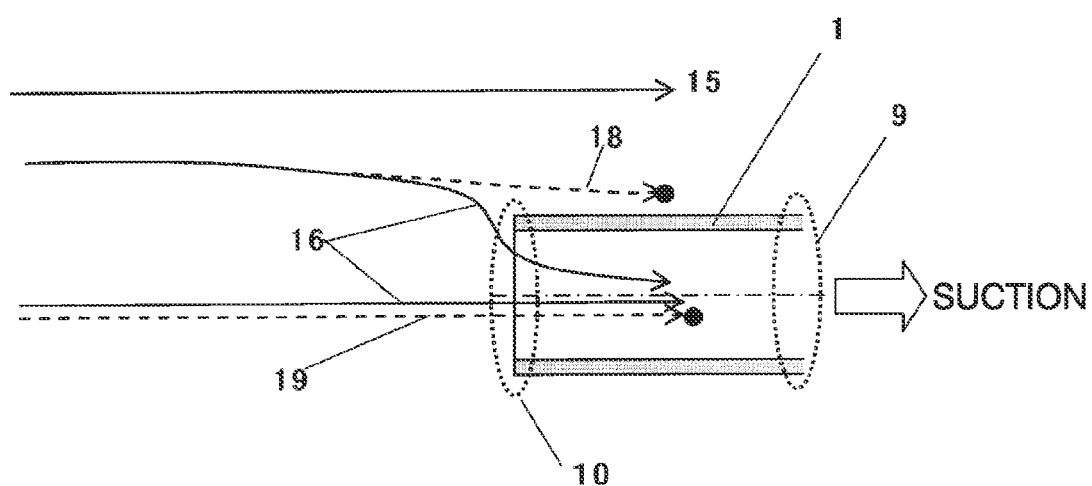
FIG. 4 is a schematic diagram of another related art.
Figure 5:
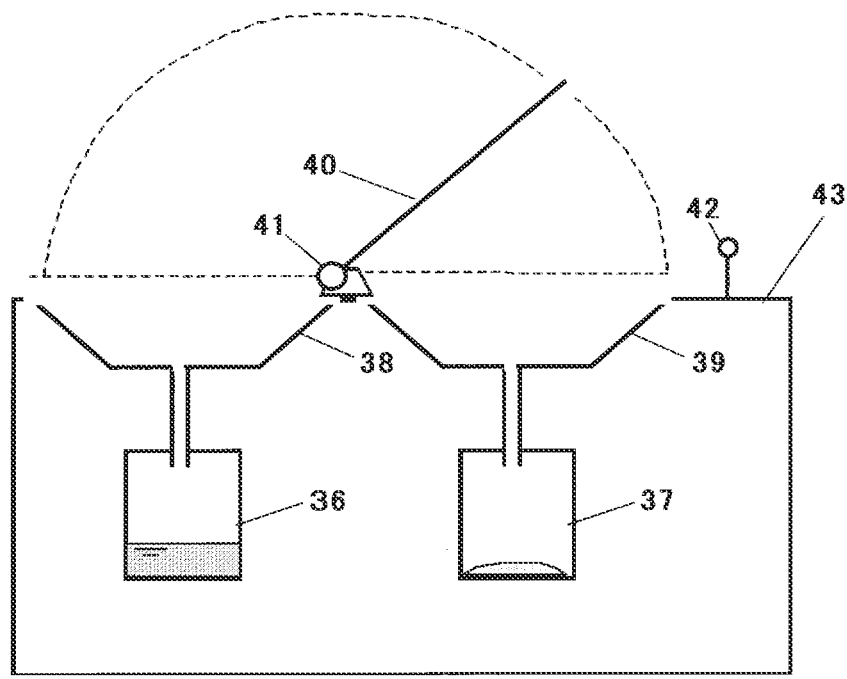
FIG. 5 is a schematic diagram of another related art.

Hereinafter, preferred embodiments of the invention will be described in detail by referring to the accompanying drawings. Furthermore, in the specification and the drawings, the same reference numerals will be given to the components having substantially the same functional configurations, and the repetitive description thereof will be omitted.

[First Embodiment]

Hereinafter, a first embodiment of the invention will be described by referring to FIGS. 8 to 10C.

A device (called a continuous dust amount measurement device 6) according to the invention includes a dust sampling port 1, an air pipe 5, and a trap container 25. External air and dustfall in the external air naturally flow into the dust sampling port 1 by the wind in the external air. The dust sampling port 1 is connected to the air pipe 5 at an air port 9. A part or all dustfall inside the dust sampling port 1 falls inside the dust sampling port 1 and is trapped in the trap container 25 through the air pipe 5.

(Dust Sampling Port 1)

The dust sampling port 1 will be described by referring to FIGS. 9A to 9D and FIGS. 10A to 10C. The dust sampling port 1 includes a partition plate 4, a ceiling plate 3, and a side wall 2 provided with the external air inlet 10.

(Side Wall 2 of Dust Sampling Port 1)

The side wall 2 is a substantially conical (trumpet-shaped) plate of which the upper and lower ends are opened about the center axis corresponding to the vertical direction. The side wall 2 has a shape which is widened upward. Typically, the side wall 2 has a configuration in which a portion corresponding to a side surface of a truncated cone having a center axis corresponding to a vertical line is formed as a plate. The shapes of the upper and lower bottoms of the truncated cone may be a circular shape or a shape which is similar to a circular shape such as a regular polygon having at least four or more apexes. For example, when the upper and lower bottoms have a circular shape, the shape of the side wall 2 becomes a side surface of a circular truncated cone. Further, the horizontal cross-section of an arbitrary height of a space surrounded by the side wall 2 is a circular shape or a shape similar to a circular shape such as a regular polygon. Furthermore, the center of the horizontal cross-section or the center is positioned on the same vertical line at all times. The cross-sectional area of the horizontal cross-section monotonously increases from the lower end of the circular truncated cone toward the upper end thereof.

Furthermore, a protrusion (for example, a head of a fixed bolt) or an opening (for example, a port or the like) sufficiently smaller than the area of the plate may be present on the plate surface. It is desirable that the area of the opening or the protrusion be, for example, the cross-sectional area less than 10% of the area of the plate. Likewise, in the embodiment, since the substantially conical side wall 2 is employed, the dustfall trapping efficiency of the dust sampling port 1 may be less dependent on the direction of the wind. From this viewpoint, it is desirable that the side wall 2 have an axisymmetric shape. However, due to convenience in processing, the sufficient effect may be obtained even when the horizontal cross-section is a shape similar to a circular shape such as a regular polygon or a shape in which anisotropy within a horizontal plane is comparatively small. For example, the horizontal cross-section may have a regular hexagonal shape, a regular octagonal shape, a regular dodecagonal shape, a hexadecagonal shape, or the like, and the anisotropy decreases as the number of angles of the horizontal cross-section increases.

The open portion of the lower end of the side wall 2 is the air port 9, and is connected to the air pipe 5. A part of the dustfall flowing into the dust sampling port 1 sinks along the slope of the side wall 2, reaches the air port 9, and is suctioned by the air pipe 5. It is desirable that the inclination of the side wall 2 be at least 45° or more and desirably 65° or more with respect to the horizontal plane. In this case, when the average inclination of the side wall 2 with respect to the horizontal plane is sufficiently large and dust sinks in the dust sampling port 1, most of the dustfall is suctioned to the air pipe 5 without adhering to the side wall 2. On the other hand, when the inclination with respect to the horizontal plane is drastically large, the axial length of the dust sampling port 1 becomes longer and the surface area increases, which is not disadvantageous from the viewpoint of the adherence of the dustfall to the wall surface. Thus, it is desirable that the inclination of the side wall 2 with respect to the horizontal plane be 85° or less.

It is desirable that the thickness of the side wall 2 be at least 10 mm or less and desirably 3 mm or less. In this case, the thickness of the side wall 2 is sufficiently small and the air passage resistance of the external air inlet 10 provided in the side wall 2 becomes smaller, so that the external air sufficiently flows into the dust sampling port 1. On the other hand, in the case of the extremely thin side wall 2, a problem such as resonance occurs since the side wall 2 is vibrated by wind, and thus it is desirable that the thickness of the side wall 2 be 0.3 mm or more.

It is desirable that the material of the inner surface of the side wall 2 be metal, glass, or ceramics in order to prevent the dustfall from adhering to the wall surface due to static electricity. Further, it is desirable that the inner surface of the side wall 2 be smooth in order to suppress the adherence of the dustfall. From this viewpoint, when the material of the inner surface of the side wall 2 is metal, stainless steel, aluminum, aluminum alloy, steel subjected to a corrosion preventing surface treatment such as zinc plating or chrome plating, copper, coppery alloy, magnesium alloy, titanium, titanium alloy, and the like may be used. Further, when ceramics are used for the inner surface of the side wall 2, china or stoneware may be used in order to prevent the dustfall from adhering to the inner surface of the side wall 2 due to moisture absorption to the inner surface. When glass is used for the inner surface of the side wall 2, soda glass, lead glass, or silica glass may be used.

Since the side wall 2 receives strong wind at the outdoor place and is exposed to sunshine or rainfall, the side wall 2 needs to have strength and weather resistance. From this viewpoint, as the structure material of the side wall 2, metal such as steel, alloy steel, aluminum, aluminum alloy, copper, copper alloy, magnesium alloy, titanium, or titanium alloy, ceramics such as china or stoneware, glass such as soda glass, lead glass, or silica glass, or rigid synthetic resin such as rigid vinyl chloride or acrylic may be used.

A plurality of the external air inlets 10 as openings of the side wall 2 is provided at a constant height near the upper end of the side wall 2 so as to have the same shape and be disposed at the same interval in the circumferential direction. The upper end of the external air inlet 10 may be equal to the upper end of the side wall 2 or may be a position lower than the upper end of the side wall 28. Since the height of the upper end of the external air inlet 10 is derived from the limitation in height of the lower end of the external air inlet 10 and the limitation in total area of the external air inlet 10 to be described later, the height of the upper end of the external air inlet 10 may be appropriately determined within the limitation range. It is desirable that the axial position of the lower end of the external air inlet 10 be in the distance within ⅕ of the height of the side wall 2 in the axial direction of the side wall 2 at the upper end of the side wall 2 in order to improve the dustfall trapping characteristics.

It is desirable that the shape of the external air inlet 10 be symmetrical in the circumferential direction in order to reduce the dependence of the dustfall trapping efficiency with respect to the direction of the wind, and a shape such as a circular shape, an oval shape, a rectangular shape, a trapezoid shape, or an isosceles triangular shape may be used. The external air inlets 10 need to be disposed at the symmetrical position with respect to the axial direction and have the same shape in order to reduce the dependence of the dustfall trapping efficiency with respect to the direction of the wind.

The number of the external air inlets 10 needs to be four or more and desirably eight to thirty six. This is because of the result of the examination performed by the inventor. When the angle formed between the direction of the wind and the vector projected to the horizontal plane of the vertical unit vector with respect to the opening of the external air inlet 10 is 35° or more, it is proved that the amount of the wind flowing into the dust sampling port 1 at the same wind speed drastically decreases so that the dustfall trapping efficiency is degraded. For this reason, when the number of the external air inlets 10 is three or less, the angle formed between the direction of the wind and the external air inlet 10 at a certain external air inlet 10 becomes 35° or more so that wind may be generated in the direction thus drastically decreasing the dustfall trapping efficiency. As the number of the external air inlets 10 increases, the influence of the direction of the wind is reduced.

However, as described below, there is a desirable maximum value in the maximum area of the external air inlet 10 and the trappable dustfall amount increases as the total area increases up to the maximum area. For this reason, the total area of the external air inlet 10 may be set to a condition approximate to the maximum area. At this time, when the number of the external air inlets 10 increases, the effective opening area for each external air inlet 10 decreases. For this reason, when the number of the external air inlets 10 is large, a problem arises in that an intake air resistance increases so that the dustfall trapping efficiency reduces, whereby a problem may occur when a large number of external air inlets 10 are provided.

It is desirable that the outer end surface of the external air inlet 10 be metal, glass, or ceramics in order to prevent the dustfall from adhering to the wall surface due to the separation of the introduced atmosphere. Further, it is desirable that the inner surface of the side wall 2 be smooth in order to suppress the adherence of the dustfall. From this viewpoint, when the material of the inner surface of the side wall 2 is metal, stainless steel, aluminum, aluminum alloy, steel subjected to a corrosion preventing surface treatment such as zinc plating or chrome plating, copper, coppery alloy, magnesium alloy, titanium, titanium alloy, and the like may be used. Further, when ceramics are used for the inner surface of the side wall 2, china or stoneware may be used in order to prevent the dustfall from adhering to the inner surface of the side wall 2 due to moisture absorption to the inner surface. When glass is used for the inner surface of the side wall 2, soda glass, lead glass, or silica glass may be used. Since the side wall 2 receives strong wind at the outdoor place and is exposed to sunshine or rainfall, the side wall 2 needs to have strength and weather resistance. From this viewpoint, as the structure material of the side wall 2, metal such as steel, alloy steel, aluminum, aluminum alloy, copper, copper alloy, magnesium alloy, titanium, or titanium alloy, ceramics such as china or stoneware, glass such as soda glass, lead glass, or silica glass, or rigid synthetic resin such as rigid vinyl chloride or acrylic may be used. It is desirable that the outer end surface of the external air inlet 10 be chamfered in order to reduce degradation of the dustfall trapping efficiency due to the separation of the introduced atmosphere.

(Ceiling Plate 3 of Dust Sampling Port 1)

The ceiling plate 3 comes into contact with the upper end of the side wall 2 so that the center axis thereof is aligned with the center axis of the side wall 2 in the side wall 2.

The ceiling plate 3 needs to be a substantial disk in order to reduce the dependency with respect to the direction of the wind. The "substantial disk" indicates a structure in which the ceiling plate within the horizontal plane has small anisotropy and is thin. Specifically, it is desirable that the ceiling plate 3 be a disk. However, a shape similar to a circular shape such as a regular polygon having at least four or more apexes may be employed when convenience in processing or the like is considered. Further, the ceiling plate may be formed in a circular dome shape having a gentle inclination (that is, thin in the vertical direction) in consideration of drainage performance on the ceiling plate in the case of rainfall. For example, a circular dome in which the maximum inclination of the dome is 10° or less may be applied. In the case of a structure in which the ceiling plate is thick in the vertical direction, it is not desirable in that the air resistance of the ceiling plate becomes larger so that the external air flowing into the dust sampling port is disturbed.

The material of the ceiling plate may be any type as long as the material has strength capable of maintaining the structure at the outdoor place and does not permit the permeation of rainwater. Specifically, the material applicable to the side wall 2 may be applied to the ceiling plate 3. Further, the end surface of the ceiling plate may have an acute angle or a streamline shape in order to reduce air resistance.

(Partition Plate of Dust Sampling Port)

Figure 10A:
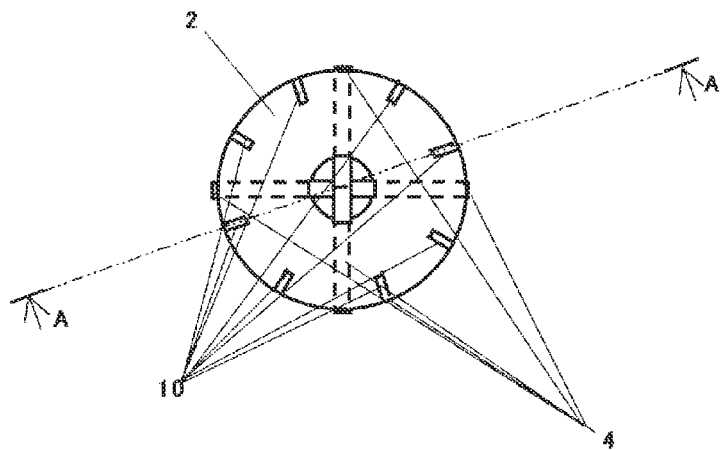
FIG. 10A is a schematic plan view of a flow field inside the particle sampling port of FIGS. 9A to 9D.
Figure 10B:
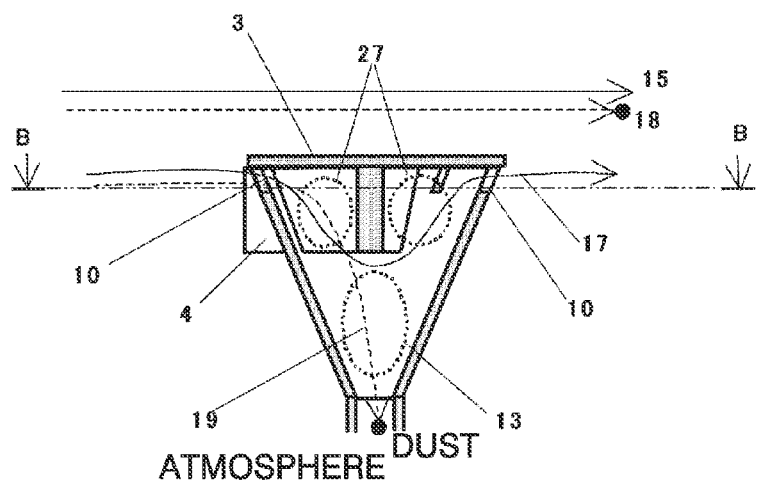
FIG. 10B is a schematic cross-sectional view of the flow field.
Figure 10C:
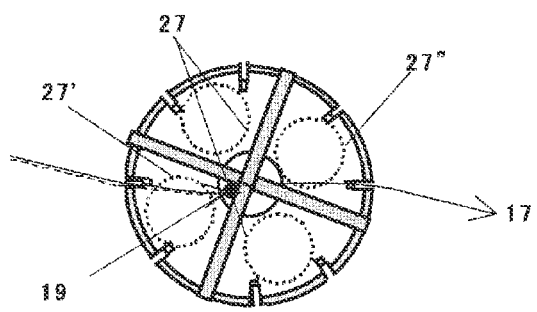
FIG. 10C is another schematic cross-sectional view of the flow field.

The partition plate 4 comes into contact with the upper portion of the side wall 2 including the ceiling plate 3 and the upper end of the side wall 2, and the partition plates are disposed so that the end surfaces thereof come into contact with each other at the center axis of the dust sampling port 1. As a result, the upper portion inside the sampling port is divided into small areas 27 each having a fan-shaped horizontal cross-section and having the external air inlet 10 and a downward opening. The partition plates 4 are installed so that a plurality of the fan-shaped small areas 27 having the same cross-sectional shape is disposed in the circumferential direction of the dust sampling port. Here, when the number of the fan-shaped small areas 27 is three or less, most of the atmosphere flowing from the upstream external air inlet to the fan-shaped small area in the wind of the external air enters around the lower end of the partition plate 4 as shown in FIGS. 10A to 10C, and directly flows outward from the downstream external air inlet of the same fan-shaped small area without passing through a wind reduction area 13. As described above, since the atmospheric dustfall is separated and condensed at the wind reduction area, there is a problem in that the ratio of the dustfall reaching the air port 9, that is, the dustfall trap ratio is low when the number of the fan-shaped small areas 27 is three or less.

On the other hand, when the number of the fan-shaped small areas 27 is four or more, most of the atmosphere flowing from the external air inlet of the fan-shaped small area 27' in the atmosphere enters around the lower end of the partition plate 4 and passes through the wind reduction area 13. Subsequently, the inward flowing air flows outward into the external air from the fan-shaped small area 27" different from the fan-shaped small area 27 into which the atmosphere flows or falls into the air port to be trapped in the trap container. The inventor found that most of the atmospheric dustfall in the wind reduction area 13 is separated from the outward flowing atmosphere and is suctioned to the air port 9 in the meantime, so that high dustfall trapping efficiency is obtained.

Figure 12:
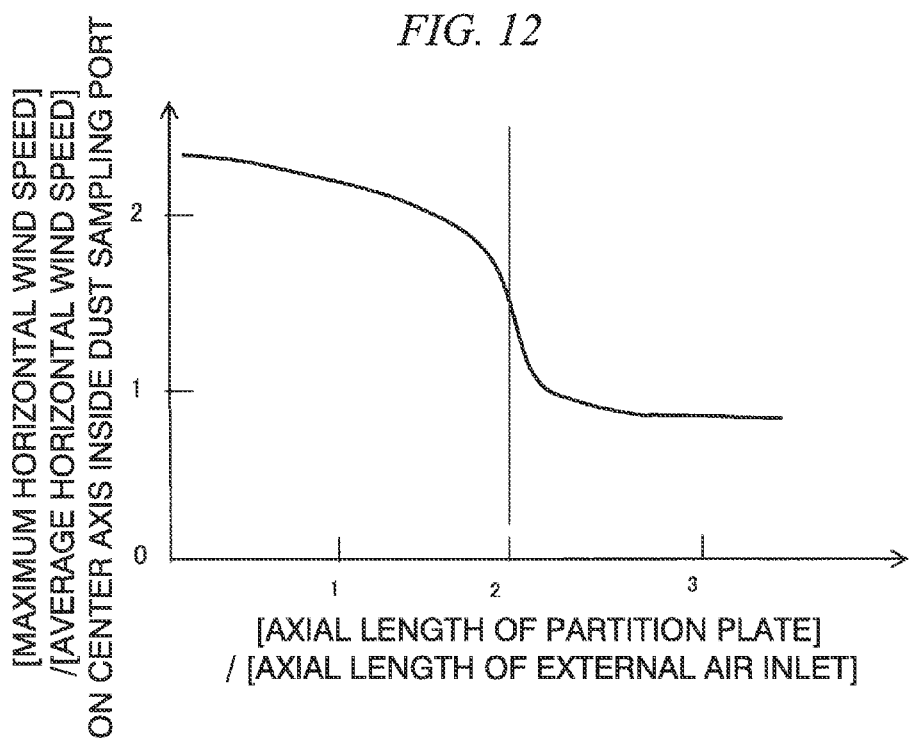
FIG. 12 is another schematic diagram relating to an effect of the embodiment.

Therefore, the number of the fan-shaped small areas 27 needs to be four or more, and in order to realize this, the number of the partition plates needs to be four or more. Further, one or more external air inlets needs to be essentially present at the fan-shaped small area 27 so that the external air directly flows into the fan-shaped small area. Since there is a minimum value in the desirable cross-sectional area of the external air inlet 10, the total area obtained by adding the cross-sectional areas of all external air inlets 10 increases as the number of the fan-shaped small areas increases. As described below, since there is a maximum value having a desirable range in the total area of the external air inlet 10, there is a desirable maximum value in the number of the fan-shaped small areas, that is, the number of the partition plates. As a result of the examination of the inventor, it is desirable that the number of the fan-shaped small areas, that is, the number of the partition plates be sixteen or less. It is desirable that the axial length of the partition plate 4 be twice or more of the axial length of the external air inlet 10. In this case, as shown in FIG. 12 which is a result of the examination of the inventor, the maximum horizontal wind speed/the average horizontal wind speed on the center axis inside the dust sampling port 1 is not largely more than 1. That is, no blowing occurs in the horizontal direction inside the dustfall sampling port 1, and the dustfall trapping efficiency drastically improves.

Figure 13:
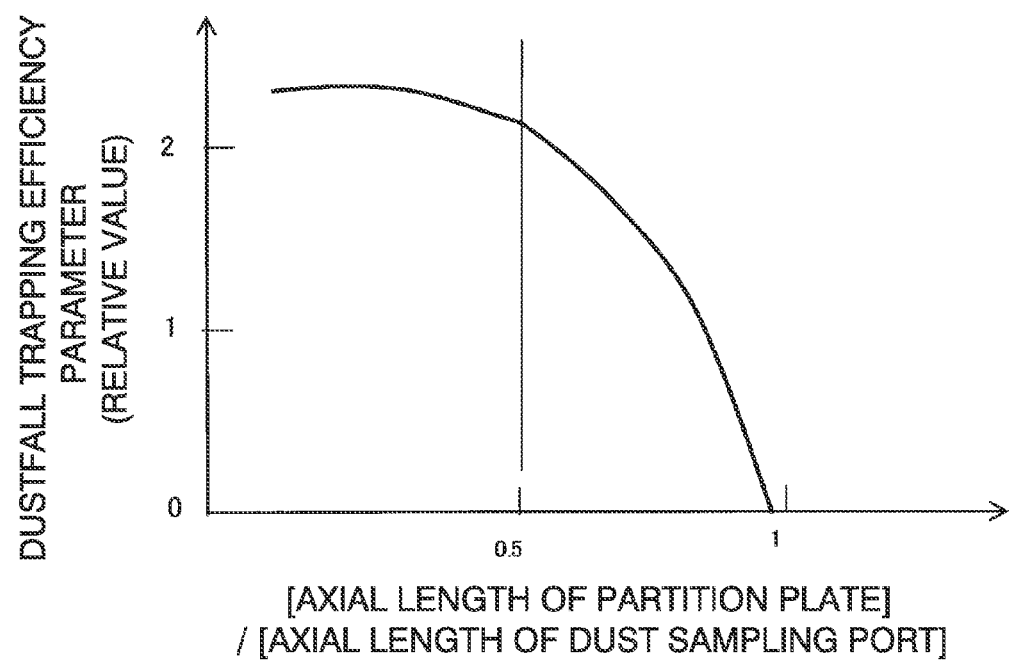
FIG. 13 is another schematic diagram relating to an effect of the embodiment.
Figure 14A:
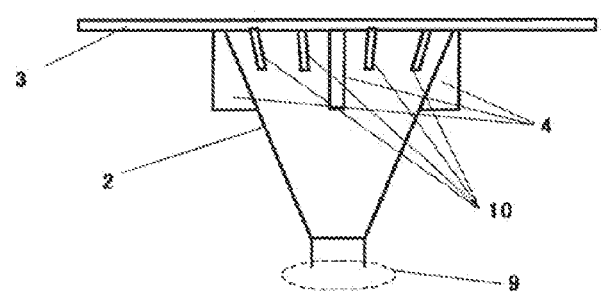
FIG. 14A is a schematic diagram and a side view of a second embodiment of the invention.
Figure 14B:
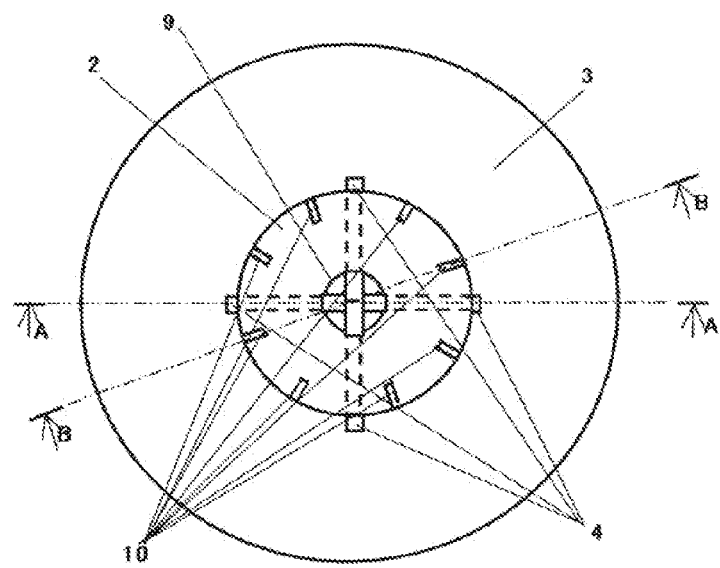
FIG. 14B is a schematic plan view of the embodiment.
Figure 14C:
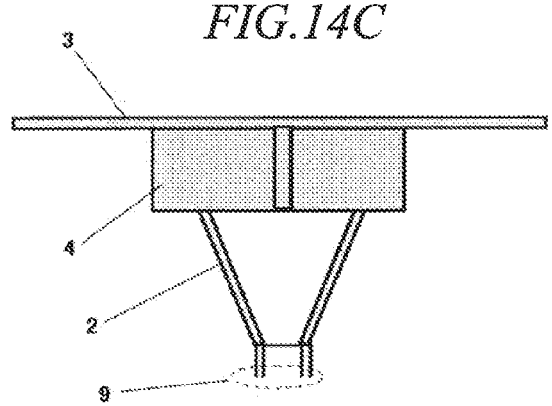
FIG. 14C is a schematic cross-sectional view taken along the line A-A of FIG. 14B.
Figure 14D:
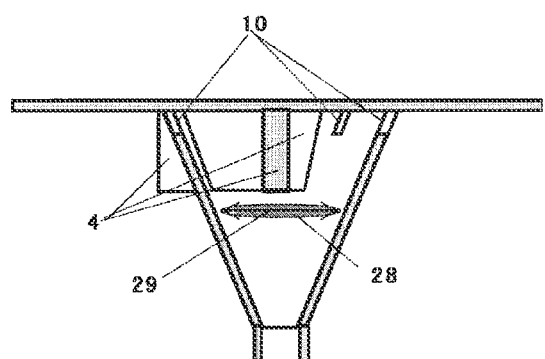
FIG. 14D is a schematic cross-sectional view taken along the line B-B of FIG. 14B.

Further, it is desirable that the axial length (height) of the partition plate 4 be the same at each partition plate 4 and be 0.5 times or less the axial length of the dust sampling port 1. As shown in FIG. 13, which is a result of the examination of the inventor, in this case, a dustfall trapping efficiency parameter P1 (which will be defined later) to be described later of the dust sampling port 1 becomes sufficiently larger. For this reason, the dustfall trapping efficiency is sufficiently high. That is, the dustfall trapping efficiency in the dust sampling port 1 becomes higher as the dustfall trapping efficiency parameter P1 becomes larger. In particular, when the axial length of the partition plate 4 is set to be extremely long to be equal to the axial length of the dust sampling port 1, the air passage resistance largely increases due to the partition plate 4 inside the dust sampling port 1 as another problem other than a degradation of the dustfall trapping efficiency parameter P1. Accordingly, the amount of the external air flowing into the dust sampling port extremely decreases, so that the dustfall trapping efficiency degrades.

Hereinafter, the value of [axial length of partition plate 4]/[axial length of dust sampling port 1] is denoted by L1. Further, the value of [axial length of partition plate 4]/[axial length of the external air inlet 10] is denoted by L2.

Further, referring to FIG. 13, the reason why the tendency of the characteristic curve changes from the boundary when L1 is 0.5 will be described. The blowing inhibiting effect becomes higher as L2 becomes larger, whereas the area of the external air inlet may easily decrease and the trapped dustfall amount may easily decrease. For this reason, L2 is designed to be about 2 as an appropriate lower limit value in many cases.

In such a condition, the dustfall trapping efficiency parameter P1 is substantially constant when L1 is 0.5 or less as shown in FIG. 13. On the contrary, when L1 becomes more than 0.5, the dustfall trapping efficiency parameter P1 rapidly decreases. The reason why the dustfall trapping efficiency parameter P1 decreases when L1 is 0.5 or more is because the space inside the dust sampling port which may become the wind reduction area 13 decreases. The reason why the dustfall trapping efficiency parameter P1 becomes constant at 0.5 or less is because of the following reasons.

When L1 is small, the space inside the dust sampling port which may become the wind reduction area 13 is wide, but there is a high wind speed area since the uniformity of the wind speed in the vertical direction is not sufficient. For this reason, the upper end of the wind reduction area 13 is fairly below the lower end of the partition plate 4. Since the wind speed in the vertical direction becomes uniform as L1 increases to approach 0.5, the gap between the upper end of the wind reduction area 13 and the partition plate 4 decreases. As a result, the upper end of the wind reduction area 13 becomes constant in the area where L1 is 0.5 or less. As a result, even when L2 is set to be smaller, the wind reduction area does not extend in the axial direction and the dustfall trapping efficiency parameter P1 becomes a substantially constant value. Furthermore, even when the wind speed in the vertical direction has a distribution in this area, the blowing in the horizontal direction does not occur in the case of the dust sampling port 1 where L2 is in the range of the appropriate condition.

On the other hand, as described above, when L1 becomes more than 0.5 in FIG. 13, the dustfall maintenance parameter rapidly decreases as in the case of FIG. 13. Therefore, the value of 0.5 is important as a limit value in which L1 does not have an adverse influence on the dustfall trapping efficiency.

As a connection form between the partition plate 4 and the ceiling plate 3, the upper end surface of the partition plate 4 is connected to the lower side of the ceiling plate 3 without any gap formed therebetween or the partition plate 4 penetrates the ceiling plate 3 without any gap in the penetration portion. As a connection form between the side wall 2 and the ceiling plate 3, the outer end surface of the partition plate 4 is connected to the inner surface of the ceiling plate 2 without any gap formed therebetween or the partition plate 4 penetrates the side wall 2 without any gap formed in the penetration portion. Furthermore, in the connection form between the ceiling plate 3 and the partition plate 4 in FIGS. 9A to 9D, the upper end of the partition plate 4 is connected to the lower surface of the ceiling plate 3 without any gap formed therebetween. Further, in the connection form between the side wall 2 and the partition plate 4, the partition plate 4 penetrates the side wall 2 without any gap formed therebetween.

Further, in the fixation through such a connection, a method such as welding, adhering, or threading may be used. Further, a sealing material such as a silicon sealant or grease may be applied in order to suppress the inflow and outflow of the atmosphere by preventing a gap at the connection portion. As the material of the partition plate, any type may be used as long as the material may maintain its structure and has no air permeability and low adherability of dustfall. For example, the same material as that of the above-described side wall 2 may be used.

(Trap Container)

The trap container 25 may have any structure as long as the trapped dustfall may be easily extracted without discharging the trapped dustfall into the external air again. The same structure as that of the related art may be applied to the trap container 25. For example, a glass bottle for a deposit gauge as the related art may be used. It is desirable that the volume of the trap container be sufficiently large in consideration of the case where water obtained from rainfall flows from the dust sampling port 1 into the trap container for a measurement period. For example, the volume of 10 L may be used. As the material of the trap bottle, stainless steel, aluminum, corrosion-preventive steel, or the like may be used instead of glass.

The trap container 25 may be adapted to be extracted from the air pipe 9, and after dustfall is trapped for a predetermined period, the trap container 25 may be extracted from the air pipe 9 so as to collect the trapped dustfall.

In order to prevent foreign matter from being mixed with the trap container 25, it is desirable that the connection portion between the trap container 25 and the air pipe 9 be sealed. However, for convenience of the attachment and detachment of the trap container, a structure may be adopted in which a narrow gap is provided between the trap container 25 and the air pipe.

The trapped dustfall may be prevented from flying apart again by inserting water into the trap container 25. In this case, when trapping the dustfall, dustfall as an insoluble solid is filtered and collected, and a water-soluble dustfall liquid is collected together with the water. The collected filtered residual material and the residual material obtained by drying a filtered liquid respectively correspond to insoluble dustfall and soluble dustfall. Further, in the state where water is not inserted into the trap container 25, the dustfall may be trapped and the insoluble dustfall and the soluble dustfall may be collected as a solid. When the mass of the dustfall obtained in this manner is measured by, for example, an electronic balance, the total mass of the dustfall, the mass of the insoluble dustfall, and the mass of the soluble dustfall may be obtained.

Furthermore, strictly, particles such as more minute SPM are contained in the trap container other than the dustfall. In an environment in which the concentration of the mass of the SPM particles is sufficiently smaller than the concentration of the mass of the dustfall, the mass of the dust trapped in the trap container may all be regarded as the mass of the dustfall. Further, when the concentration of the mass of the SPM may not be ignored, for example, a filtering may be performed by using a filter permitting the permeation of 10 µm or less of particles so as to separate the trapped dustfall from the trapped SPM after trapping the dust.

(Dustfall Trapping Mechanism of Dust Sampling Port 1)

A dustfall trapping mechanism inside the dust sampling port 1 of the embodiment will be described. In the embodiment, the atmospheric dustfall flowing from the external air inlet 10 flows into the wind reduction area 13 together with the atmosphere when the introduced atmosphere bypasses the partition plate 4 and passes the downside of the partition plate 4. When the dustfall flows into the wind reduction area 13, in the downward vertical direction due to the effect of changing the direction of the ambient atmospheric flow to the downward vertical direction or the effect of causing the dustfall particle to collide with the partition plate 4 the dustfall accelerates. For this reason, for example, a particularly large dustfall particle having a diameter of 100 µm or more directly falls to the air port 9, and is trapped in the trap container 25 through the air pipe 5. A part of the dustfall particle which is not particularly large freely falls while staying inside the wind reduction area 13, and reaches the air port 9 as in the larger dustfall particle so as to be trapped in the trap 25 through the air pipe. As described in the BSNE which is the related art, the effect of the wind reduction area with respect to the trap of the dustfall is that the larger amount of dustfall is trapped downward compared to the case where the wind reduction occurs by extending the staying time of the dustfall inside the dust sampling port 1.

Next, the dustfall trapping efficiency parameter P1 contrived by the inventor will be defined by the following equation.

[dustfall trapping efficiency parameter P1]=[wind reduction area horizontal cross-sectional area 28]×[wind reduction area length 29]/[total area of external air inlet 10]$^2$ Here, the wind reduction area indicates an area where the wind speed of the atmosphere containing the dustfall flowing from the external air inlet 10 at the flow wind speed in the dust sampling port 1 is reduced. Further, the wind reduction area horizontal cross-sectional area 28 indicates a maximum value of the horizontal cross-section of the wind reduction area 13. Furthermore, the wind reduction area length 29 indicates a length of a path where air passes the wind reduction area. When the external air is not directly discharged from the dust sampling port 1, the wind reduction area indicates a distance from the boundary near the external air inlet of the wind reduction area to the air port. When the external air is directly discharged from the dust sampling port 1 as in the BSNE, the wind reduction area indicates a length of a line connected from the boundary near the external air inlet of the wind reduction area to the exhaust port 8 or the downstream external air inlet 10 (in the case of the embodiment). In order to recognize the specific position of the wind reduction area and the specific length of the wind reduction area, for example, the low wind speed area may be distinguished by obtaining a distribution of the wind speed inside the dust sampling port 1 using a flow meter disposed inside the dust sampling port 1.

Further, the physical meaning of the dustfall trapping efficiency parameter P1 will be described. In the external air flowing into the dust sampling port 1 at a specific speed, the average staying time of the atmosphere and the atmospheric dustfall in the wind reduction area increases in proportion to [cross-sectional area of external air inlet 10]/[wind reduction area horizontal cross-sectional area 28]. Further, as the value of [wind reduction area length 29]/[cross-sectional area of external air inlet 10] becomes larger, the uniformity of the wind speed in the wind reduction area 13 more improves. That is, the effect of preventing a reduction in rapid blowing through only a part of the wind reduction area 13 from the boundary near the external air inlet 10 to the exhaust port 8 or the air port 10 becomes higher as the value of [wind reduction area length 29]/[cross-sectional area of external air inlet 10] becomes larger. Since the blowing phenomenon significantly shortens the average staying time of the atmospheric dustfall in the wind reduction area 13, the trapping efficiency is largely degraded. Therefore, the state where the dustfall parameter is large may be regarded as a state where the dustfall trapping efficiency due to the free falling dustfall becomes higher since the atmospheric dustfall usually stays in the wind reduction area 13 for a long time. Therefore, as the dustfall trapping efficiency parameter P1 becomes larger, the dustfall trapping efficiency in the dust sampling port 1 becomes higher. That is, the dustfall trapping efficiency in the specific dust sampling port may be organized by using the dustfall trapping efficiency parameter P1.

Figure 11:
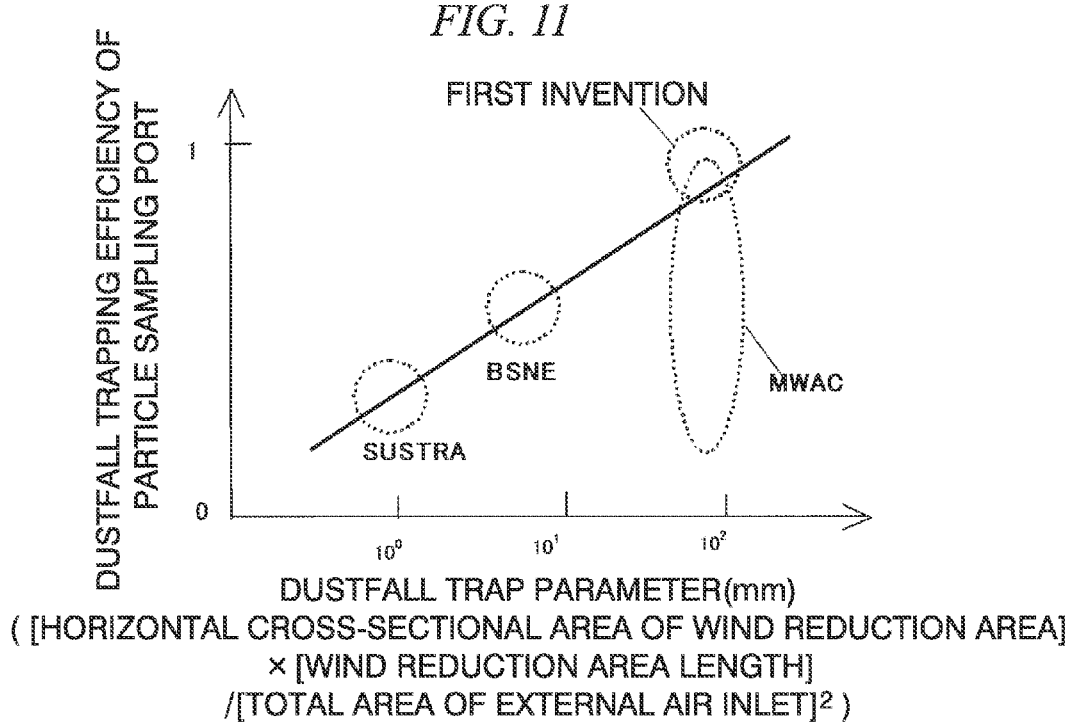
FIG. 11 is a schematic diagram relating to an effect of the embodiment.

The relationship between the dustfall trapping efficiency parameter P1 and the dustfall trapping efficiency in the horizontal dustfall component trap will be more specifically described. Since the wind reduction area 13 of the BSNE or the SUSTRA is comparatively smaller than the opening area of the external air inlet, the dustfall trapping efficiency parameter P1 is also small. For this reason, as shown in FIG. 11, the dustfall trapping efficiency is smaller than, for example, the maximum value of the dustfall trapping efficiency in the MWAC.

The MWAC may indicate that the value of the dustfall trapping efficiency parameter P1 is comparatively large and at this time, the value of the dustfall trapping efficiency is high. However, the MWAC has a large defect in which the dependency of the dustfall trapping efficiency with respect to the wind direction of the external air is extremely strong. This defect is caused by the following reason. Since the vicinity of the opening of the external air inlet 10 of the MWAC is formed in a direct pipe, the atmosphere flowing into the external air inlet needs to have the axial speed of the direct pipe immediately after it flows thereinto. For this reason, when the axial direction of the external air inlet 10 is different from the wind direction of the external air, the flow resistance increases due to the abrupt change in direction of the atmosphere in the external air inlet 10, the inflow amount of the external air decreases, and the flow of the dustfall in the external air may not follow the abrupt change in direction of the inflow atmosphere, so that the amount of the dustfall flowing into the external air inlet 10 decreases. For this reason, in the MWAC, the dustfall trapping efficiency largely changes in accordance with the wind direction. In the MWAC, only when the wind direction of the external air is equal to the direction of the external air inlet, the dustfall trapping efficiency is high.

In the embodiment, since the external air inlets 10 are intermittently present in the circumferential direction of the dust sampling port 1, the value of the dustfall trapping efficiency parameter P1 may be set to be larger than that of the device of the related art. When there is a need to obtain the maximum efficiency of the MWAC and the dustfall trapping efficiency, the value of the dustfall trapping efficiency parameter P1 may be set to about 100 [1/mm] This corresponds to a case where eight external air inlets 10 with a width of 3 mm and a height of 7 mm are provided at the upper end of, for example, an available trumpet-shaped reducer with an upper end diameter of 45 mm and a height of 60 mm. The dimensions of the trumpet-shaped reducer and the external air inlet 10 may be appropriately set so as to satisfy the condition necessary for the dustfall trap parameter.

Further, in the embodiment, most of the surface of the dust sampling port 1 is not opened. Compared to the other type in which the opening is large, the dust sampling port 1 of the embodiment has a large air resistance with respect to the ambient atmosphere. For this reason, a large negative pressure is generated at the surface of the dust sampling port 1 in the downward wind direction. As a result, a force is exerted on the external air inlet 10 in the downward wind direction so that the atmosphere inside the dust sampling port 1 is suctioned to flow outward. For this reason, even when the external air inlet 10 is relatively small and there is a difference between the direction of the external air inlet and the wind direction of the external air, the ventilation of the dust sampling port 1 is not particularly degraded. For example, even in the MWAC, although the opening area of the atmosphere inlet 10 is comparatively small, in the case of the device, a particular pressure reduction condition does not occur in the vicinity of the exhaust port 8 in the downward wind direction. For this reason, the ventilation of the dust sampling port 1 may be expected only by the effect of making the external air flow into the external air inlet 10 on the basis of the inertia of the flow of the external air. For this reason, in the MWAC, the ventilation efficiency of the dust sampling port 1 is easily degraded, which corresponds to a large factor of degrading the dustfall trapping efficiency.

Since the dust sampling port for the SPM system shown in FIG. 6 suctions the external air, it cannot be classified as the horizontal dustfall component trap, but has a common point with the structure of the embodiment in that the structure is axisymmetric, the ceiling plate is provided, and the structure (cone) disturbing the flow is present below the ceiling plate inside the dust sampling port. In the case of using the dust sampling port, the wind reduction area 13 is formed below the structure 14 disturbing the conical flow. However, since the area with the opening is large in the entire circumference of the external air inlet, the value of the dustfall trapping efficiency parameter P1 is small. Further, since most of the atmosphere flowing from the external air inlet 10 into the dust sampling port 1 takes a flow 17 bypassing the structure disturbing the flow in the horizontal direction, the ratio of the atmosphere actually flowing into the wind reduction area is low. For this reason, in the dust sampling port of FIG. 6, the dustfall trapping efficiency is small, and is not suitable as the dustfall sampling port. In the SPM system, it is an object to trap only the SPM by separating the SPM from the large dustfall which may freely fall in the atmosphere. For this reason, in the SPM system, it is natural that the dustfall trapping efficiency of the dust sampling port 1 is low.

(Method of Calculating Horizontal Dustfall Amount Flux)

The horizontal dustfall amount flux value may be calculated by dividing the dustfall amount measured by the continuous dust amount measurement device 6 per hour by the effective opening area of the external air inlet. The effective opening area of the external air inlet of the embodiment indicates a sum of the projection area to the perpendicular plane with respect to the wind direction in the opening area into which the external air actually flows in the external air inlet. In order to specify the opening into which the external air flows, for example, it may be determined whether the external air flows into each external air inlet by measuring the flow field near the dust sampling port 1 under a constant wind speed condition after disposing the device in a wind tunnel.

Further, generally, the average flow speed of the external air at the opening of the external air inlet becomes smaller than the wind speed of the external air due to the air resistance of the dust sampling port. As a result, the mass of the dustfall flowing into the dust sampling port together with the external air also reduces compared to the case where the external air flows into the dust sampling port at the wind speed of the external air. That is, the dustfall trapping efficiency at the dust sampling port is generally lower than 100%. Therefore, when calculating the horizontal dustfall amount flux, the horizontal dustfall amount flux value may be corrected by dividing the horizontal dustfall amount flux calculated in advance by the above-described method by the dustfall trapping efficiency obtained in advance. As a method of obtaining the dustfall trapping efficiency in advance, for example, the device is disposed inside the wind tunnel, a constant concentration of a specific type of dustfall is discharged from the upstream for a constant time, and at this time, the dustfall trapping efficiency is calculated by using the mass of the dustfall trapped in the device per hour, the external air inlet effective opening area obtained by the above-described method, and the average value of the horizontal dustfall amount flux inside the wind tunnel. That is,

[dustfall trapping efficiency]=[mass of dustfall trapped by device per hour]/([external air inlet effective opening area]×[average value of horizontal dustfall amount flux inside wind tunnel])

may be established.

The average value of the horizontal dustfall amount flux inside the wind tunnel may be obtained by the method or the like disclosed in Non-patent Document 2.

Further, in the embodiment, the amount of the trapped dustfall is proportional to the horizontal flux of the amount of the dustfall in the external air regardless of the wind speed of the external air. Therefore, when the absolute value of the horizontal dustfall amount flux is not needed for the purpose of managing the tendency of the horizontal dustfall amount flux, the standard value of the dustfall amount measurement value in the device of the embodiment is determined in advance, and the relative horizontal dustfall flux may be obtained by dividing the dustfall amount measurement value obtained in time-series in the continuous dust amount measurement device 6 of the embodiment by the standard value.

[Second Embodiment]

A second embodiment will be described by referring to FIGS. 14A to 14D. The embodiment has the same structure as that of the first embodiment except for the ceiling plate. In the embodiment, the diameter of the ceiling plate 3 needs to be larger than the diameter of the upper end of the side wall 2. When the diameter of the ceiling plate 3 is equal to the diameter of the upper end of the side wall 2, any size of raindrop flowing onto the dust sampling port 1 in the case of rain may flow from the external air inlet 10 into the dust sampling port 1. At this time, the dustfall received in the raindrop due to the washing-out effect of the rainfall flows into the dust sampling port 1 together with the raindrop as a wet deposit so as to be trapped in the trap container 25. The influence of the dustfall as the wet deposit with respect to the environment is different from that of the dustfall as a dry deposit which is trapped in the case of no rain.

For example, when the dustfall as the wet deposit contains soluble salt or acid, such a material in the rainfall may affect vegetation or the like as a growth degradation factor. On the other hand, even when soluble acid is contained in the dry deposit, the vegetation is hardly affected immediately after the dustfall is deposited.

In the device according to the embodiment, the diameter of the ceiling plate 2 is larger than the diameter of the upper end of the side wall 2. In this case, the outer portion of the ceiling plate in relation to the upper end of the side wall 2 serves as a peak portion, and in the case of rain with a raindrop having a specific dimension or more, the raindrop is suppressed from intruding into the dust sampling port 1. As the diameter of the ceiling plate 3 becomes larger, the smaller raindrop may be suppressed from intruding into the dust sampling port 1. That is, in the embodiment, the trap of the wet dustfall deposited together with a raindrop having a specific minimum diameter or more may be suppressed.

However, on the other hand, the maximum diameter of the raindrop which may flow into the dust sampling port 1 in the case of no rain becomes smaller as the diameter of the ceiling plate becomes larger, and there is a problem in that the dry dustfall having a specific minimum diameter or more deposited in the case of no rain may not be trapped. Therefore, when the range of the value of the diameter of the ceiling plate is determined on the basis of two equations below, the horizontal dustfall component trap, that is, the horizontal component trap for the dustfall as the dry deposit may be realized which does not trap the dustfall as the wet deposit in the case of the rainfall while trapping the dustfall as the dry deposit in the desired dimension range.

[radial length of peak portion of ceiling plate]<[representative wind speed of external air]/[free falling speed of dustfall which is desired to be trapped]×[vertical length between lower surface of ceiling plate and lower end of external air inlet]

Further,

[radial length of peak portion of ceiling plate]>[representative wind speed of external air]/[free falling speed of raindrop which is not desired to be trapped and has the smallest diameter]×[vertical length between lower surface of ceiling plate and lower end of external air inlet]

Generally, the diameter of the raindrop is 300 μm or more, whereas the diameter of the representative dustfall is 100 μm or less. Therefore, the length of the peak portion of the ceiling plate 3 applied to the horizontal component trap for the dustfall as the dry deposit may be realized.

Furthermore, the dustfall which is not received in the raindrop in the case of rain flows into the dust sampling port together with the wind of the external air. Such dustfall may be regarded as a dry deposit. Further, in the case where there is a sufficient density of the raindrop, for example, in the case of the rainfall of 1 mm or more for one hour, the washing-out effect of the dustfall is large, and the influence of the dry deposit in the case of the rain is ignorably small.

It is desirable that the ceiling plate be a disk in order to reduce the dependence of the wind direction, but when convenience in processing is considered, the ceiling plate may have a shape similar to a circular shape such as a regular polygon. Further, when the horizontal cross-section of the side wall 2 has a shape other than a circular shape, for example, a regular polygonal shape, the diameter of the circumscribed circle with a regular polygonal shape of the cross-section of the side wall at the upper end of the side wall may be set to the diameter of the upper end of the side wall 2. Furthermore, when the ceiling plate 3 has a shape other than the circular shape, for example, a regular polygonal shape, the diameter of the inscribed circle of the ceiling plate 3 may be set to the diameter of the ceiling plate 3.

[Third Embodiment]

A third embodiment of the invention will be described by referring to FIG. 15. In the drawing, in a first horizontal dustfall component trap 32, the diameter of the ceiling plate 3 is equal to the diameter of the upper end of the side wall 2, and the horizontal components of the dustfall as a dry deposit and the dustfall as a wet deposit may be trapped. In a second horizontal dustfall component trap 33 installed on a trestle to be adjacent to the first horizontal dustfall component trap 32, the diameter of the ceiling plate 3 is larger than the diameter of the upper end of the side wall 2, and only the dustfall as a dry deposit is trapped. That is, the mass of the dustfall trapped in the second horizontal dustfall component trap 33 may be set as the amount of the dry deposit material of the horizontal component of the dustfall. Since the two horizontal dustfall component traps are installed at the same height to be adjacent to each other, it is considered that the tow horizontal dustfall component traps are exposed to the same horizontal dustfall flux in the external air.

Therefore, the mass of the dustfall of the remainder obtained by reducing the mass of the dustfall trapped in the second horizontal dustfall component trap 33 from the mass of the dustfall trapped in the first horizontal dustfall component trap 32 may be set as the amount of the wet deposit material of the horizontal component of the dustfall. In this manner, the amounts of the wet deposit and the dry deposit of the horizontal component of the dustfall may be separately measured.

Furthermore, when obtaining a difference in mass between the dustfalls trapped in the first and second horizontal dustfall component traps for obtaining the mass of the wet deposit, not only the total mass is used, but also a difference in mass between the dustfalls trapped in both traps is obtained depending on each component of the dustfall, each particle diameter of the insoluble particle, or water solubility, so that the amount of the wet deposit material may be obtained in accordance with the component of the dustfall, the particle diameter distribution, or the soluble/insoluble state. Regarding the dry deposit trapped in the second horizontal dustfall component trap 33, when the trapped material is collected, the trapped material is dissolved in water, the mass of the filtered and dried material is measured off-line, and the amount of the dry deposit material for the soluble/insoluble state may be obtained. By this method, the horizontal component of the dustfall may be analyzed while being simply separated into the soluble wet deposit, the insoluble wet deposit, the soluble dry deposit, and the insoluble dry deposit. As a result, information helpful for the environmental management may be obtained.

EXAMPLES

Example 1

Figure 8:
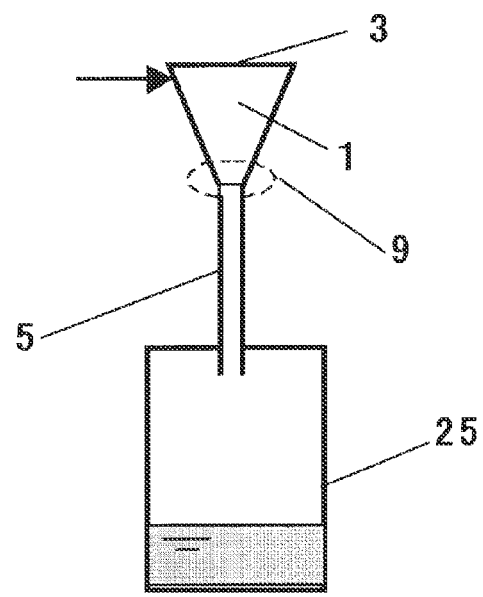
FIG. 8 is a schematic diagram of a first embodiment of the invention.
Figure 9A:
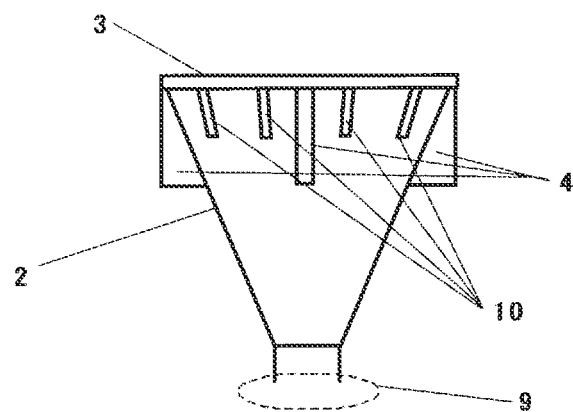
FIG. 9A is a schematic side view of a particle sampling port of the embodiment.
Figure 9B:
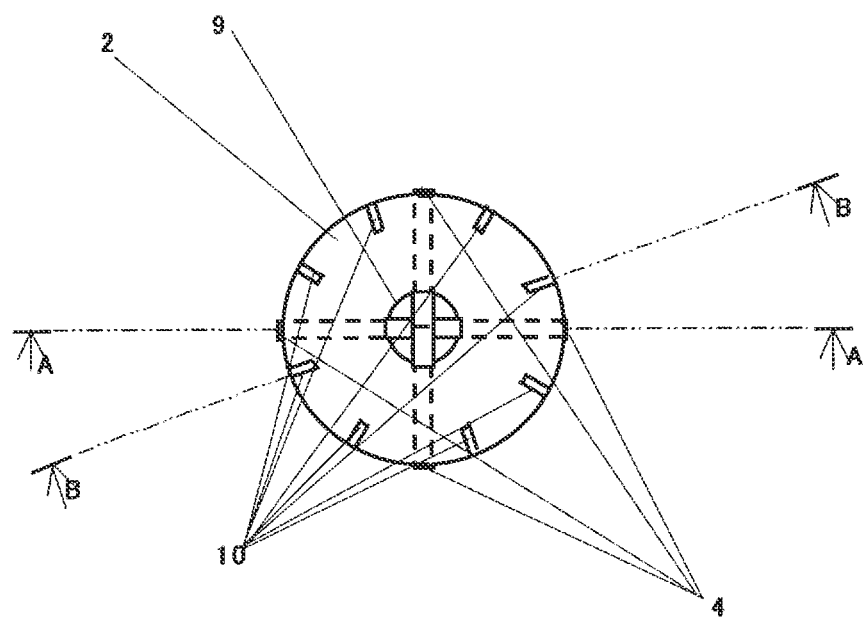
FIG. 9B is a schematic plan view of the particle sampling port of the embodiment.
Figure 9C:
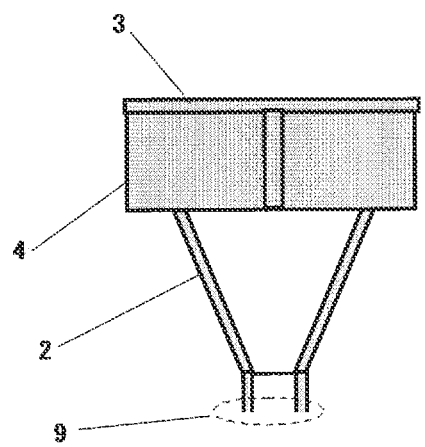
FIG. 9C is a schematic cross-sectional view of the particle sampling port of the embodiment.
Figure 9D:
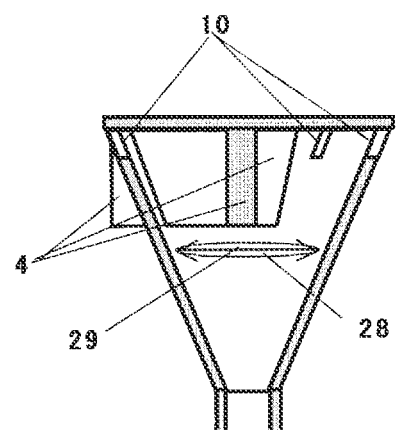
FIG. 9D is a schematic cross-sectional view of the particle sampling port of the embodiment.

The horizontal flux of the dustfall was continuously measured outdoors by using a device configured by applying the dust sampling port with the structure shown in FIG. 9 to the configuration of FIG. 8.

As the side wall 2 of the dust sampling port 1, a reducer (with an outer diameter of an upper end of the reducer: 48 mm, an outer diameter of a lower end: 21.7 mm, and an axial length: 63 mm) of the stainless reducer 5K, 1-½×½ according to Japanese Industrial Standards (JIS) was used. The external air inlet 10 was formed by processing eight openings (with a rectangular shape) in the circumferential direction from the upper end of the side wall 2 so as to have a width of 3 mm and a height of 7 mm. In the same manner, four notches were processed in the circumferential direction from the upper end of the pipe wall so as to have a width of 4 mm and a depth of 25 mm. The partition plate 4 was formed by inserting four stainless steel plates with a width of 24 mm, a length of 24 mm, and a thickness of 4 mm into the notches. The partition plate was threaded into the ceiling plate 3 as a stainless disk with a diameter of 48 mm and a thickness of 2 mm. An epoxy-based resinous adhesive was used for the connection between the ceiling plate 3 and the upper end of the side wall 2 and between the side wall 2 and the partition plate 4, so that they were bonded and sealed.

A stainless pipe having a diameter of 1 inch was welded to the lower end of the side wall 2, that is, the air port 9, and a stainless pipe having an outer diameter of 6 mm was welded to the lower end of the stainless pipe with a stainless reducer interposed therebetween, so that these stainless pipes were used as the air pipe 5. The air pipe 5 was inserted into a mouth of the trap container 25 as a narrow mouthed bottle having a volume of 20 L and formed of glass, and an attachable and detachable rubber packing was filled between the outside of the air pipe 5 and the inside of the mouth of the trap container 25, so that the air pipe 5 adhered to the trap container 25. The trap container was filled with water in advance, both a solid material and a soluble material inside the trap container were collected when collecting the trapped material, a dry material of a residual material obtained by filtering the collected material was set as the amount of the horizontal component of the insoluble dustfall, and the mass thereof was measured. Further, in the filtered liquid, the mass of the residual material obtained by evaporating water therefrom was measured, and this value was set as the trapped amount of the horizontal component of the horizontal dustfall.

The total mass value of the trapped amount of the horizontal component of the insoluble dustfall and the trapped material of the horizontal component of the soluble dustfall was set as the trapped amount of the horizontal component of the dustfall, and the value was divided by the time of the experiment period and 50 $mm^2$ of the effective opening area of the external air inlet obtained by the experiment in advance so as to calculate the horizontal dustfall flux. Furthermore, in the experiment of calculating the effective opening area of the external air inlet, the experiment was performed as below on the basis of the standard low speed wind tunnel experiment method described in JSME Mechanical Engineers' Handbook A5 (Japan Society of Mechanical Engineers). The device of the embodiment with the dust sampling port manufactured by using a transparent acrylic material and having the same shape as that of the outdoor experiment was installed in the wind tunnel, and the wind speed of the wind tunnel was set to be constant.

A tuft (a string for observing an air flow) was installed behind each external air inlet inside the dust sampling port of the device, and the wind direction was measured according to the tuft method. In the tuft method, the direction indicated by the front end of the tuft corresponds to the momentary downward flow (the air flow direction) of the air flow. The motion of the front end of the tuft was observed from the upside through the transparent ceiling plate, and the air flow direction indicated by the front end of the tuft was continuously recorded. The air flow direction was classified into two directions, that is, the inflow direction and the outflow direction with respect to the external air inlet, and each time ratio indicated by the front end of the tuft was calculated. The external air inlet in which the time ratio of the air flow direction becoming the inflow direction with respect to the external air inlet was more than half was set to the effective opening.

The sum of the projection areas with respect to the plane perpendicular to the wind direction of all effective opening in any experiment condition was set to the effective opening area in the experiment condition. The wind tunnel experiment was performed plural times by changing the condition of the angle formed between the wind direction and the external air inlet and the wind speed condition, and the average value in the total experiment conditions of the effective opening areas respectively obtained from the experiments was adopted as the representative effective opening area.

The method of the outdoor experiment is as below. The device was installed on a work desk positioned at the height of 5 m from the ground so as to be present in a position where no tall barrier was provided in the range of 200 m around the device by selecting a day with no rainfall, and continuous measurement was performed for twelve hours. For comparison, a high volume sampler, capable of manually changing the direction of the air port and the air suction flux, and an aerovane were installed adjacent to the device, and the uniform suction was manually maintained during the experiment by using these. That is, the momentary measurement value of the aerovane was visually checked, and then an operation was normally performed in which the direction of the air port of the high volume sampler was manually made to match the wind direction measurement value and the air suction flux of the high volume sampler was made to match the wind speed measurement value. The dust trap filter of the high volume sampler was exchanged every hour so as to manually measure the mass thereof off-line, whereby the dustfall trap mass per hour was obtained. The dustfall trap mass was divided by the time (one hour) and the air port opening area of the high volume sampler so as to be converted into the horizontal dustfall flux at the corresponding trapping time. Furthermore, a preliminary survey was performed at the measurement value point of this Example, and it was checked in advance that the concentration of the mass of the SPM in the atmosphere at the corresponding point was sufficiently smaller than the concentration of the mass of the dustfall. Therefore, in this Example, the dust trap amount of each measurement device was set to the dustfall trap amount.

This experiment was performed ten times on different days. The dustfall trapped in the trap container of the device was collected after the end of each experiment. When water was not accumulated inside the container due to the natural evaporation during the measurement, the mass of the dustfall was directly measured. Further, when water was accumulated in the container, the moisture of the collected material was evaporated in a depressurized state, and the mass of the residual material was measured as the mass of the dustfall.

As a result, the horizontal dustfall flux measurement value obtained by dividing the mass (mass) of the dustfall trapped per hour in the device by the external air inlet opening area was 0.14 mg/m$^2$ s in average. On the contrary, a difference between the measurement value of each experiment day of the device and the average measurement value of each day using the high volume sampler was 0.021 mg/m$^2$ s in average, and the standard deviation was small so as to be 0.012 mg/m$^2$ s. Then, it was found that the device was able to perform a uniform suction and a highly precise horizontal dustfall flux measurement.

Here, a method of calculating the effective opening area of the external air inlet will be specifically described. The effective opening area was set to the sum of the projection areas to the perpendicular plane with respect to the wind direction of the opening into which external air flowed in the external air inlet. In order to specify the opening into which the external air flows, the device was disposed inside the wind tunnel, wind with a constant wind speed was applied from the side surface thereof, and the wind directions near sixteen external air inlets were measured. This result was set to the subject for calculating the effective area of the external air inlet having a direction in which the external air flows into the dust sampling port in average. As a result of the measurement in various wind direction conditions, the effective opening area of the external air inlet was 1.6 times the opening area of each external air inlet in average.

Furthermore, the dust amount measurement using the uniform suction through the high volume sampler has high precision, but there are problems in that the direction of the device and the suction flow rate need to be manually changed from the device and basically the arrangement type trap filter needs to be manually and frequently exchanged. Therefore, in fact, it is not appropriate to apply the above-described method to the continuous measurement of the horizontal dustfall component for a long period of time from the viewpoint of labor cost. On the contrary, in the device and the method according to the embodiment, as described above, a highly precise result is obtained without performing a manual operation.

Example 2

Prepared was a horizontal dustfall flux measurement device having a dust sampling port with a structure shown in FIGS. 14A to 14D, the ceiling plate 3 with a diameter of 150 mm, and a configuration of FIG. 8. The horizontal dustfall flux was continuously measured at the outdoor place by using the device. A high volume sampler as a comparative dust trap was further provided with a rain detector, an external air inflow opening cover, and a cover opening and closing device, and then a mechanism automatically opening and closing the external air inflow opening cover was further provided so that the external air was not suctioned in the case of rain. By using this mechanism, the high volume sampler was able to suction the dust only in the case of no rain. In the state where the other structures were the same as those of Example 1, the experiment was performed ten times on different days.

As a result, the horizontal dustfall flux measurement result calculated in the same manner as that of Example 1 was 0.10 mg/m$^2$ s in average in the device. On the contrary, a difference between the measurement value of each experiment day of the device and the average measurement value of each day using the high volume sampler was 0.013 mg/m$^2$ s in average and the standard deviation thereof was small so as to be 0.008 mg/m$^2$ s. As a result, it was found that the device was able to highly precisely measure the horizontal dustfall flux in the case of no rain.

Further, in this example, the free falling speed of the dustfall which was desired to be trapped was 0.2 m/s, and the minimum free falling speed of the raindrop which was not desired to be trapped was 1.5 m/s. Because it is drizzle in the case of the falling speed or less, a large amount of rainfall may not occur in general. The representative wind speed of a region where the measurement was performed was set from 2 to 10 m/s. The minimum representative wind speed was set due to the reason that the horizontal dustfall component was not a problem at the wind speed or less. As the maximum representative wind speed, the maximum wind speed at the region in an average year was adopted. That is, there was a need to provide a trap capable of trapping the necessary dustfall even in the case of the minimum representative wind speed and not trapping the raindrop having a size (a free falling speed) which was desired to be excluded even in the case of the maximum representative wind speed. In the precondition, the diameter of the ceiling plate 3 was set so that the length of the peak portion of the ceiling plate of the embodiment was in the desirable range described in the second embodiment.

Further, as a result of examining the material collected in the device when there was strong rainfall of 10 mm per hour and the average wind speed during the rainfall was close to the maximum representative wind speed, it was found that the rainwater trapped in the trap was 10 ml and most of the rainfall was excluded from the device. On the contrary, for example, in the trap of Example 1, several hundreds or more ml of rainwater was trapped in general with respect to 10 mm of rainfall.

Further, in another experiment in which the wind speed is a value approximate to the minimum representative wind speed value through all experiment periods, the collected material of the device was examined. As a result, it was found that the trapped material contained 8% or more of dustfall having a free falling speed of 0.2 m/s or more and desired to be trapped. As a result, it was found that the device was able to efficiently trap the dustfall having a size (a free falling speed) desired to be trapped. Furthermore, in order to examine the free falling speed of the trapped material, the trapped material was made to fall from an upper portion of a clean dark room, and an experiment was performed to specify a momentary particle position from scattering light by allowing the dropped particle to be irradiated with a sheet-like laser beam. By using this method, the falling speed of the particle was calculated from a time necessary for the fall of each particle.

Furthermore, when determining the dimension of the device of the Example, a preliminary experiment was performed by changing the condition of the device in a manner such that (a) the axial length of the partition plate 4 was set to 7 mm or (b) the axial length of the partition plate 4 was set to 80% (50.4 mm) of the axial length of the dust sampling port, and an appropriate condition was found. When the axial length of the partition plate 4 was extremely short, the dustfall trapping efficiency was degraded due to blowing (for example, 40%). Further, when the axial length of the partition plate 4 was extremely long, the trapping efficiency was degraded due to a decrease in the wind reduction area (for example, 30%).

Comparative Example 1

Figure 6A:
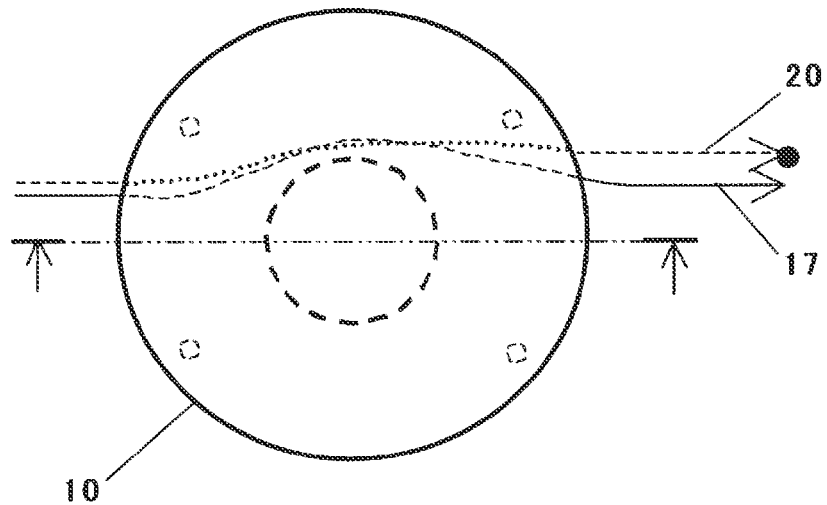
FIG. 6A is a schematic plan view of another related art.
Figure 6B:
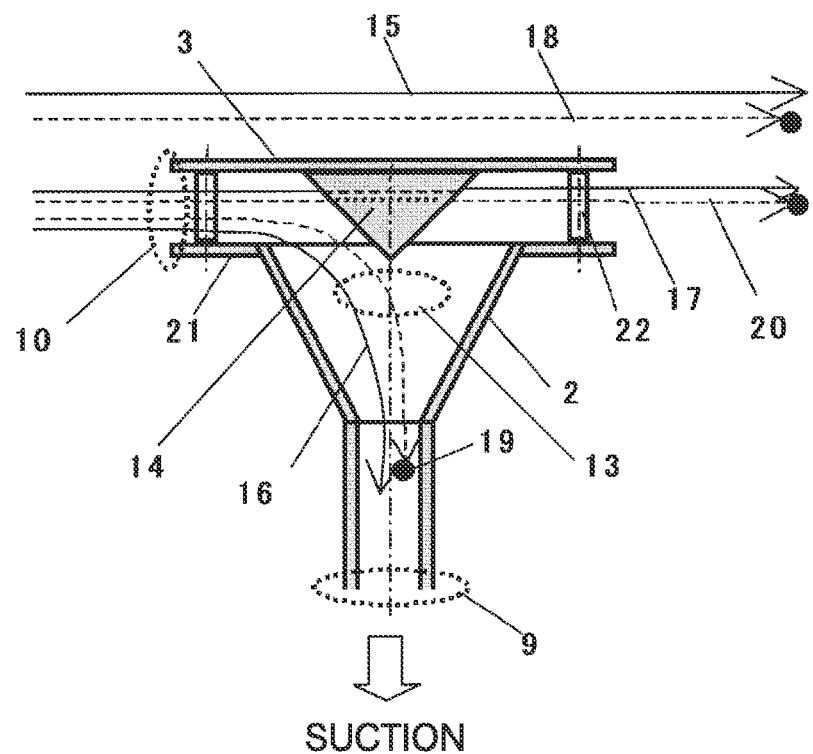
FIG. 6B is a schematic cross-sectional view of another related art.
Figure 7A:
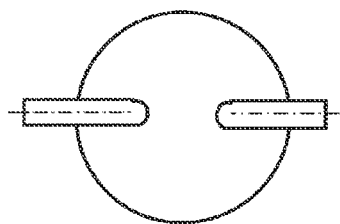
FIG. 7A is a schematic plan view of another related art.
Figure 7B:
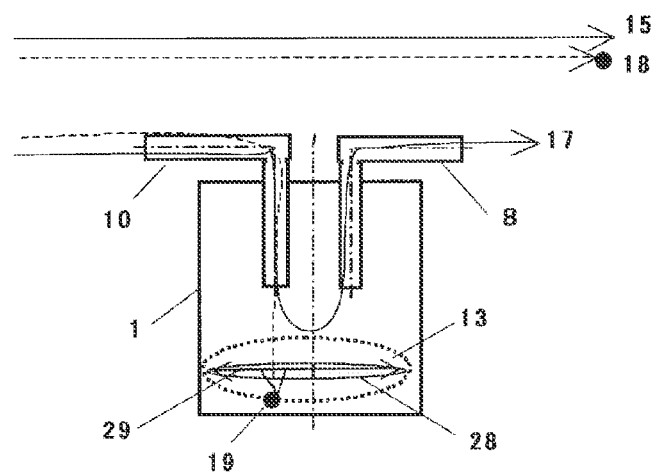
FIG. 7B is a schematic cross-sectional view of another related art.

A dust trap was manufactured in which the dust sampling port was set to the dust sampling port with a structure of the related art shown in FIGS. 6A and 6B and the trap container was connected to the downside of the dust sampling port, and the experiment was performed in the state where the other conditions were the same as those of Example 2. The dustfall trap mass measurement value measured by the device was compared with the dustfall trap mass measurement value of the high volume sampler performing the uniform suction as a comparative measurement device provided in parallel to the device. In the comparison of both measurement values, a difference in effective opening area of the external air inlet 10 of the dust sampling port 1 between the high volume sampler and the device was reflected. That is, when the dustfall trapping efficiency of the device was 100%, the dustfall trap mass measurement value using the high volume sampler was corrected so that the dustfall trap mass measurement value of the device was equal to the dustfall trap mass using the high volume sampler. Furthermore, when obtaining the effective opening area of the external air inlet, since the device had a single opening in the entire circumference, the wind tunnel experiment was performed, and the portion into which the external air flowed inside the external air inlet was obtained. Such an experiment was performed ten times on different days.

As a result, in the horizontal dustfall flux measurement result calculated in the same method as that of Example 1, the ratio of the measurement value of each experiment day of the device with respect to the average measurement value of each experiment day using the high volume sampler was small so as to be 0.05 in average. On the other hand, the standard deviation of the ratio was 0.15 and was larger than the average value of the ratio. That is, it was found that the order of the measurement using the device was different from that of the horizontal dustfall flux measurement value using the high volume sampler and only the measurement value having a low correlation degree was obtained. This is because the dustfall may not be highly efficiently trapped in the dust sampling port using the device as the dust sampling port of the related art.

Example 3

The dust sampling port 1 was made similar to that of Example 2 by making the twice dimension. In the state where the other conditions were the same as those of Example 2, the experiment was performed. As a result, the dustfall trap amount per hour, that is, the horizontal dustfall amount flux calculated in the same manner as that of Example 2 was about four times that of the device of Example 2.

According to these Examples, it was found that the respective embodiments of the invention may provide a horizontal dustfall component trap capable of measuring a horizontal dustfall flux with a small, simple, and cheap structure.

Example 4

Figure 15:
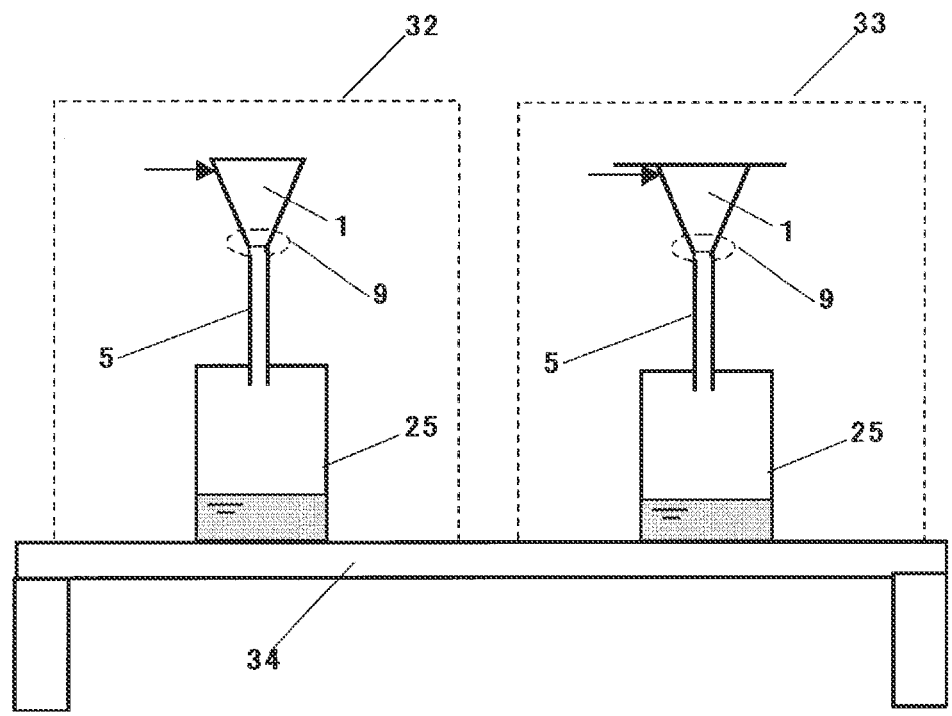
FIG. 15 is a third embodiment of the invention.
Figure 16:
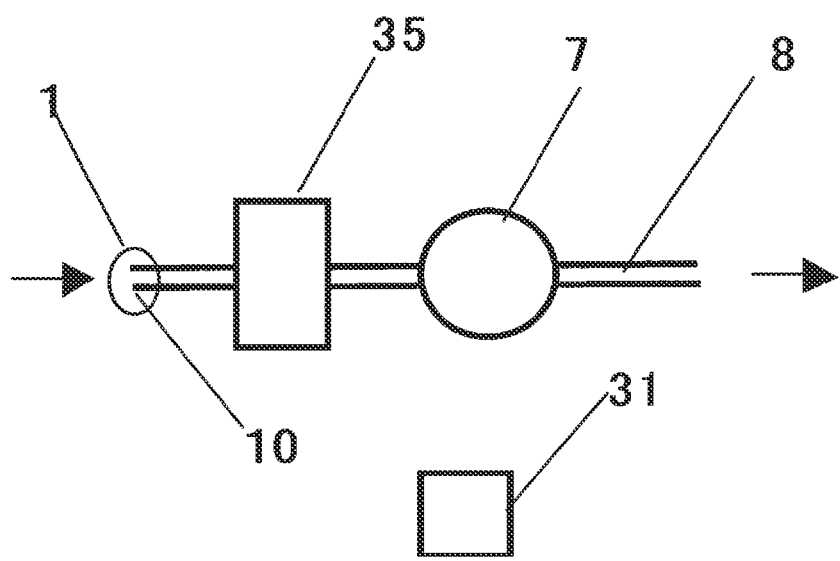
FIG. 16 is a schematic diagram of another related art.

The experiment was performed by the configuration of the device of FIG. 15. In the drawing, the first horizontal dustfall component trap is the same as the horizontal dustfall component trap used in Example 1. The second horizontal dustfall component trap is the same as the horizontal dustfall component trap used in Example 2. The two horizontal dustfall component traps were installed at an outdoor place without a barrier in the peripheral range of 200 m so as to be disposed on a trestle 34 positioned at the height of 5 m from a floor surface with a gap of 3 m therebetween. In this state, the dustfall was trapped for one month. In the meantime, there was rainfall for five days in total, and the sum of the rainfall amount was 30 mm.

After the experiment ended, the dustfall was collected together with the water inside the trap container from the trap containers of the two horizontal dustfall component traps. Each collected material was filtered, the mass of the filtered liquid was measured, the component of the filtered liquid was analyzed, and the mass composition ratio of the component was examined. Further, after the mass was measured by drying the filtered residual material, the component analysis was performed, and the mass composition ratio of the component was measured. A general ion chromatography method was used when measuring the mass composition ratio of each component of the soluble dustfall, and a general fluorescent X-ray method was used so as to obtain the mass composition ratio for each component of the insoluble dustfall.

The following equation was performed by using the mass measurement value and the component mass composition ratio measurement value using the component analysis, and the mass of each of the soluble wet deposit, the insoluble wet deposit, the soluble dry deposit, and the insoluble dry deposit was obtained. Furthermore, the entire mass of the wet deposit was calculated by summating the mass of the soluble wet deposit and the mass of the insoluble wet deposit, and the entire mass of the dry deposit was calculated by summating the mass of the soluble dry deposit and the mass of the insoluble dry deposit.

[amount of soluble dry deposit material of specific component]=[mass of filtered liquid trapped in second horizontal dustfall component trap]×[mass composition ratio of specific component of filtered liquid trapped in second horizontal dustfall component trap]

[amount of insoluble dry deposit material of specific component]=[mass of filtered residual material trapped in second horizontal dustfall component trap]×[mass composition ratio of specific component of filtered residual material trapped in second horizontal dustfall component trap]

[amount of soluble wet deposit mass of specific component]=[mass of filtered liquid trapped in first horizontal dustfall component trap]×[mass composition ratio of specific component of filtered liquid trapped in first horizontal dustfall component trap]−[mass of filtered liquid trapped in second horizontal dustfall component trap]×[mass composition ratio of specific component of filtered liquid trapped in second horizontal dustfall component trap]

[amount of insoluble wet deposit material of specific component]=[mass of filtered residual material trapped in first horizontal dustfall component trap]×[mass composition ratio of specific component of filtered residual material trapped in first horizontal dustfall component trap]−[mass of filtered residual material trapped in second horizontal dustfall component trap]×[mass composition ratio of specific component of filtered residual material trapped in second horizontal dustfall component trap]

Next, the horizontal flux values of the mass of the dustfall were respectively calculated by the method shown in Example 1. Among these results, the representative component had the following value.

As the soluble wet deposit, sodium chloride was 0.02 mg/m$^2$ s, magnesium chloride was 0.003 mg/m$^2$ s, calcium chloride was 0.001 mg/m$^2$ s, and sodium sulfate was 0.001 mg/m$^2$ s. These materials were calculated by the correlation with the representative chemical types from the measurement values of the amount of ion (for example, amount of $SO_4^{2-}$). For example, $SO_4^{2-}$ was correlated with sodium sulfate.

As the insoluble wet deposit, $SiO_2$ (calculated from the composition ratio of component Si) was 0.02 mg/m$^2$ s, $Al_2O_3$ (calculated from the composition ratio of component Al) was 0.005 mg/m$^2$ s, and iron oxide (calculated from the composition ratio of component Fe by assuming the chemical formula as $Fe_2O_3$) was 0.005 mg/m$^2$ s.

As the soluble dry deposit, sodium chloride was 0.003 mg/m$^2$ s and magnesium chloride was 0.001 mg/m$^2$ s.

As the insoluble dry deposit, $SiO_2$ was 0.06 mg/m$^2$ s, $Al_2O_3$ was 0.01 mg/m$^2$ s, iron oxide was 0.02 mg/m$^2$ s, and $TiO_2$ was 0.002 mg/m$^2$ s.

The entire horizontal dustfall flux of the wet deposit was obtained by summating the horizontal flux of the soluble wet deposit and the insoluble wet deposit. The entire horizontal dustfall flux of the dry deposit was obtained by summating the flux of the soluble dry deposit and the insoluble dry deposit.

Furthermore, the entire horizontal dustfall flux of the dry deposit may be calculated in a manner such that water containing the dustfall collected from the second horizontal dustfall component trap is dried, the mass of the dried dustfall is measured (measurement value A), and the measurement value A is calculated as the entire horizontal dustfall flux of the dry deposit. Further, the entire horizontal dustfall flux of the wet deposit may be calculated in a manner such that water containing the dustfall collected from the first horizontal dustfall component trap is dried, the mass of the dried dustfall is measured (measurement value B), and a value (B-A) obtained by subtracting the measurement value A from the measurement value B is calculated as the entire horizontal dustfall flux of the wet deposit.

Likewise, according to the invention, the horizontal dustfall flux of each of the soluble wet deposit and the insoluble humid deposit as a humid deposit and each of the soluble dry deposit and the insoluble dry deposit as a dry deposit which are difficult to be obtained in the related art may be simply obtained.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

INDUSTRIAL APPLICABILITY

According to the invention, it is possible to provide a horizontal dustfall component trap capable of measuring a horizontal flux of dustfall with a structure which is small, simple, and cheap. Further, according to one aspect of the invention, a horizontal dustfall component as a dry deposit and a horizontal dustfall component as a wet deposit may be separated from each other.

REFERENCE SIGNS LIST

1: dust sampling port
2: side wall
3: ceiling plate
4: partition plate
5: air pipe
8: exhaust port
9: air port
10: external air inlet
12: casing
13: wind reduction area
14: flow disturbing structure
15: atmospheric flow of external air
16: suctioned atmospheric flow
17: atmospheric flow passing into dust sampling port
18: dustfall in external air
19: trapped dustfall
20: dustfall passing into dust sampling port
21: bottom plate
22: support column
23: blade
24: rotary shaft
25: trap container
26: air pipe
27: fan-shaped small area
27': fan-shaped small area into which atmosphere flows
27": another fan-shaped small area
27': fan-shaped small area into which atmosphere flows
27": another small area
28: wind reduction area horizontal cross-sectional area
29: wind reduction area length
30: metallic mesh
31: aerovane
32: first horizontal dustfall component trap
33: second horizontal dustfall component trap
34: trestle
35: trap filter
36: wet deposit trap container
37: dry deposit trap container
38: wet deposit dust sampling port
39: dry deposit dust sampling port
40: dust sampling port cover
41: cover opening and closing mechanism and cover opening and closing control device
42: rain detector
43: casing
44: particle trap

The invention claimed is:

1. A horizontal-component trap of atmospheric dustfall comprising:
  a dust sampling port that includes a ceiling plate, a side wall, and four or more partition plates;
  an air pipe; and
  a trap container that collects dustfall, flowing from the dust sampling port, through the air pipe,
  wherein the dust sampling port is connected to the air pipe,
  wherein the air pipe is connected to the trap container,
  wherein a lower end of the side wall is provided with an air port as an opening,
  wherein the air port is connected to the air pipe, wherein the side wall is a plate that has a vertical center axis and has a side surface having a shape of a substantially circular truncated cone or a polygonal truncated cone widened upward, wherein the side wall is provided with four or more external air inlets each having an opening disposed at the same interval in the circumferential direction of the side wall and disposed at a specific height near the upper end thereof, wherein the ceiling plate has a substantially disk shape, wherein the center axis of the ceiling plate is aligned with the center axis of the side wall, wherein the ceiling plate is connected to the upper end of the side wall so as to come into contact therewith, wherein each of the four or more partition plates is a flat plate disposed in a vertical plane, wherein each of the four or more partition plates is connected to the side wall and the ceiling plate without any gap formed therebetween, wherein the four or more partition plates are connected to each other on the center axis of the ceiling plate, and wherein the four or more partition plates divide a space surrounded by the side wall into fan-shaped areas having an equal size in a horizontal cross-section.

2. The horizontal atmospheric dustfall component trap according to claim 1, wherein a diameter of the ceiling plate is larger than a diameter of the upper end of the side wall in the horizontal cross-section, and wherein the ceiling plate has a peak portion that extends outward from the upper end of the side wall in the circumferential direction.

3. The horizontal atmospheric dustfall component trap according to claim 2, wherein a radial length of the peak portion of the ceiling plate satisfies:

(the radial length of the peak portion of the ceiling plate)<(a representative wind speed of the external air)/(a free falling speed of dustfall which is desired to be trapped)×(a vertical length between a lower surface of the ceiling plate and a lower end of the air port)

and, (the radial length of the peak portion of the ceiling plate)>(the representative wind speed of the external air)/(a free falling speed of a raindrop with a minimum diameter which is not desired to be trapped)×(the vertical length between the lower surface of the ceiling plate and the lower end of the air port).

4. A horizontal atmospheric dustfall component measurement method using the horizontal atmospheric dustfall component trap according to claim 2, wherein a value obtained by dividing the amount of dustfall trapped in the horizontal component trap per hour by an effective opening area of the external air inlets is calculated as the horizontal dustfall flux.

5. The horizontal atmospheric dustfall component trap according to claim 1, wherein a diameter of the ceiling plate is equal to a diameter of the upper end of the side wall in the horizontal cross-section.

6. A horizontal atmospheric dustfall component measurement method using the horizontal atmospheric dustfall component trap according to claim 5, wherein a value obtained by dividing the amount of dustfall trapped in the horizontal component trap per hour by an effective opening area of the external air inlets is calculated as the horizontal dustfall flux.

7. A horizontal atmospheric dustfall component measurement method using the horizontal atmospheric dustfall component trap according to claim 1, wherein a value obtained by dividing the amount of dustfall trapped in the horizontal component trap per hour by an effective opening area of the external air inlets is calculated as the horizontal dustfall flux.

8. A horizontal atmospheric dustfall component trap comprising:

a first trap which is the horizontal atmospheric dustfall component trap according to claim 1; and a second trap which is the horizontal atmospheric dustfall component trap according to claim 1, wherein in the first trap a diameter of the ceiling plate is equal to a diameter of the upper end of the side wall in the horizontal cross-section, and wherein in the second trap a diameter of the ceiling plate is larger than a diameter of the upper end of the side wall in the horizontal cross-section, and the ceiling plate has a peak portion that extends outward from the upper end of the side wall in the circumferential direction.

9. A horizontal atmospheric dustfall component measurement method using the horizontal atmospheric dustfall component trap according to claim 8, comprising:

setting an amount of dustfall trapped by the second trap as an amount of a dry deposit of a horizontal dustfall component; and calculating an amount of the dustfall, which is a remainder obtained by reducing the amount of the dustfall trapped by the second trap from an amount of a dustfall trapped by the first trap, as the amount of a wet deposit of the horizontal dustfall component.

\* \* \* \* \*